United States Patent [19]

Stapley et al.

[11] 4,036,696

[45] July 19, 1977

[54] PREPARATION OF ANTIBIOTICS BY FERMENTATION

[75] Inventors: Edward O. Stapley, Metuchen, N.J.; Justo M. Mata, Madrid, Spain

[73] Assignee: Merck & Co., Inc., Rahway, N.J.

[21] Appl. No.: 695,492

[22] Filed: June 14, 1976

Related U.S. Application Data

[60] Continuation of Ser. No. 541,039, Jan. 14, 1975, abandoned, which is a continuation of Ser. No. 463,948, April 25, 1974, abandoned, which is a division of Ser. No. 331,417, Feb. 12, 1973, Pat. No. 3,914,157, which is a continuation-in-part of Ser. No. 19,496, March 13, 1070, abandoned, Ser. No. 51,319, June 30, 1970, abandoned, and Ser. No. 203,896, Dec. 1, 1971, abandoned.

[51] Int. Cl.$^2$ .............................................. C12D 9/00
[52] U.S. Cl. .................................................. 195/80 R
[58] Field of Search .................. 195/80 R, 36 C, 36 R

[56] References Cited

U.S. PATENT DOCUMENTS

| 3,801,464 | 4/1974 | Gorman et al. | 195/80 R |
|---|---|---|---|
| 3,914,157 | 10/1975 | Stapley | 195/80 R |

*Primary Examiner*—Raymond N. Jones
*Assistant Examiner*—R. B. Penland
*Attorney, Agent, or Firm*—Richard A. Thompson; Julian S. Levitt

[57] ABSTRACT

A fermentation process for preparing 7-methoxy substituted cephalosporins. The products are useful as antibiotics and exhibit activity against gram-negative and gram-positive bacteria.

4 Claims, No Drawings

PREPARATION OF ANTIBIOTICS BY FERMENTATION

This is a streamlined continuation of U.S. Ser. No. 541,039 filed Jan. 14, 1975 now abandoned; which in turn is a streamlined continuation of U.S. Ser. No. 463,948 filed Apr. 25, 1974, now abandoned; which in turn is a divisional of U.S. Ser. No. 331,417 filed Feb. 12, 1973, U.S. Pat. No. 3,914,157; which in turn is a continuation-in-part of U.S. applications Ser. No. 19,496 filed Mar. 13, 1970, now abandoned, Ser. No. 51,319 filed June 30, 1970, now abandoned and Ser. No. 203,896 filed Dec. 1, 1971, now abandoned.

One major difficulty in antimicrobial therapy is the susceptibility of many antibiotics to enzymatic degradation. Penicillin G, for example, is effective against a wide variety of gram-positive and gram-negative microorganisms but in the presence of pencillinase it is degraded to a form which is ineffective against most pathogens. Efforts to overcome this difficulty via the preparation of various derivatives have met with only limited success.

One approach to this problem has been the development of new antibiotics which contain the "cephem" nucleus characteristic of cephalosporin C. Cephalosporin C is active against both gram-negative and gram-positive bacteria and it possesses an inherent resistance to pencillinase; however, cephalosporin C is only moderately active and there exist enzymes other than penicillinase which are effective in destroying the activity of cephalosporin C and its derivatives. These enzymes are designated as cephalosporinases.

It is an object of this invention to describe a fermentation process for preparing an antibiotic mixture and individual compounds containing the "cephem" nucleus. These products exhibit individual resistance not only to penicillinase but to the cephalosporinases as well. Certain of the products exhibit an approximately balanced gram-negative and gram-positive effect, including activity in vivo against the following gram-negative organisms: *Proteus vulgaris, Proteus mirabilis, Salmonella schottmuelleri, Salmonella gallinarum, Salmonella pullorum, Escherichia coli,* and *Klebsiella pneumoniae* and in vivo activity against the following gram-positive organisms: *Staphylococcus aureus, Streptococcus pyogenes* and *Diplococcus pneumoniae.* Other products exhibit an enhanced activity against gram-negative microorganisms.

The products of this invention bear a structural relationship to the cephalosporin series of compounds; however, unlike cephalosporin C which contains only a D-5-amino-5-carboxyvaleramido moiety at position seven, the instant products also contain a 7-methoxy substituent; and, whereas cephalosporin C is substituted by acetoxymethyl at position three of the ring, the products of this invention contain a 3-carbamoyloxymethyl, 3-α-methoxy-p-sulfooxycinnamoyloxymethyl or a 3-α-methoxy-p-hydroxycinnamoyloxymethyl moiety:

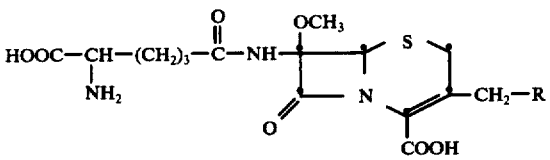

wherein R is carbamoyloxy, 60-methoxy-p-hydroxycinnamoyloxy or α-methoxy-p-sulfooxycinnamoyloxy.

Antibiotic 810A: Essentially, the products of Formula I, supra, comprise two groups of fermentation products. One of these is a mixture of compounds from which two distinct products have been isolated and identified. These two products are characterized by the presence of an α-methoxy-p-sulfooxycinnamoyloxy or an α-methoxy-p-hydroxycinnamoyloxy moiety at position 3 of the cephem nucleus:

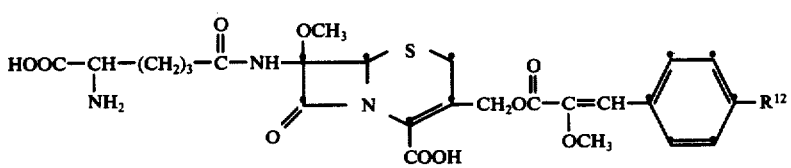

wherein $R^{12}$ is hydroxy or sulfoxy, i.e., $-OSO_3H$. These products are co-produced by cultivating under controlled conditions a new strain of actinomycete designated as MA-2837 in the culture collection of Merck & Co., Inc., Rahway, New Jersey. A sample of this culture has also been placed on permanent deposit with the culture collection of the Northern Utilization Research and Development Branch of the U.S. Department of Agriculture at Peoria, Illinois, and has been assigned the culture number NRRL 3851. Twenty-five other cultures have also been identified as producers of this antibiotic mixture (Ia) and these, together with culture MA-2837, are described infra in the section entitled THE MICROORGANISMS. Hereinafter the antibiotic mixture (Ia) comprising these two products will be referred to as Antibiotic 810A or, simply, 810A.

Antibiotic 842A: A second fermentation product comprises 7β-(D-5-amino-5-carboxyvaleramido)-3-(carbamoyloxymethyl)-7-methoxy-3-cephem-4-carboxylic acid (Ib, infra):

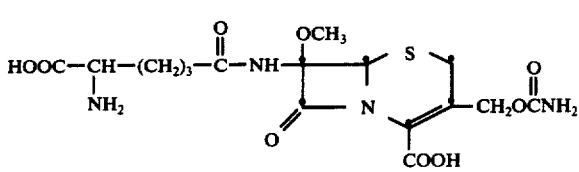

This product (Ib) is also produced by a new strain of actinomycete and a sample of this microorganism, designated as MA-2908, has been placed in the culture collection of Merck & Co., Inc., Rahway, New Jersey. A sample of this culture has also been placed on permanent deposit with the culture collection of the Northern Utilization Research and Development Branch of the U.S. Department of Agriculture at Peoria, Illinois where it has been assigned the culture number NRRL 3802. Hereinafter, in this specification, the product Ib, i.e., 7β-(D-5-amino-5-carboxyvaleramido)-3-(carbamoyloxymethyl)-7-methoxy-3-cephem-4-carboxylic acid, will be referred to as Antibiotic 842A or, simply, 842A.

ACTIVITY

One major difficulty in antimicrobial therapy is the susceptibility of most antibiotics to enzymatic degradation. Penicillin G, for example, is effective against a wide variety of gram-positive and gram-negative microorganisms but in the presence of penicillinase it is degraded to a form which is ineffective against most pathogens.

One approach to this problem has been the development of new antibiotics which contain the "cephem" nucleus characteristic of cephalosporin C. Cephalosporin C possesses an inherent resistance to penicillinase and is active against both gram-negative and gram-positive bacteria; however, it is only moderately active and there exist enzymes other than penicillinase which are effective in destroying its activity. These enzymes are designated as cephalosporinases. The products (I) of this invention demonstrate resistance not only to penicillinase but to the cephalosporinases as well. They exhibit activity against both gram-negative and gram-positive bacteria but the order of activity and the range of organisms against which they are effective is not identical.

Antibiotic 842A is characterized by an enhanced activity against gram-negative microorganisms. Unlike cephalosporin C which has a relatively low antibacterial activity, this product exhibits a significant in vivo gram-negative effect with a potency which, in general, is greater than cephalothin. This activity includes effectiveness in vivo on *Proteus morganii* and an effectiveness against the following gram-negative bacteria: *Escherichia coli, Proteus vulgaris, Proteus mirabilis, Proteus morganii, Salmonella schottmuelleri, Klebsiella pneumoniae AD, Klebsiella pneumoniae B,* and *Paracolobactrum arizonae.*

Antibiotic 842A constitutes a preferred embodiment of this invention. In addition to a generally increased gram-negative effect and an increased potency when compared to cephalothin and a greater resistance to cephalosporinases, 842A is characterized by a low order of toxicity and appears rapidly in the blood. Within four hours after administration approximately 80% is eliminated in the urine. In addition it is more resistant to enzymatic degradation than cephalosporin C and resistance to it develops slowly and it is bactericidal. Given orally it protects against infections due to *Paracolobactrum arizonae* 3270, *Proteus vulgaris* 1810, and *Salmonella schottmuelleri* 3010; and when administered subcutaneously, it is from two to 10 times more effective than cephalothin against the same infections.

Antibiotic 810A is a broad spectrum agent which exhibits an approximately balanced gram-negative and gram-positive effect. This includes activity in vivo against the following gram-negative organisms: *Proteus vulgaris, Proteus mirabilis, Salmonella pullorum, Escherichia coli,* and *Klebsiella pneumoniae* and in vivo activity against the following gram-positive organisms: *Staphylococcus aureus, Streptococcus pyogenes* and *Diplococcus pneumoniae.*

Of the several products comprising Antibiotic 810A the 7β-(D-5-amino-5-carboxyvaleramido)-3-(α-methoxy-p-sulfooxycinnamoyloxymethyl)-7-methoxy-3-cephem-4-carboxylic acid species, corresponding to Formula Ia, supra, wherein R is sulfooxy, and the salts thereof such as the sodium salt, constitutes a preferred embodiment of this invention. This product has the following planar formula:

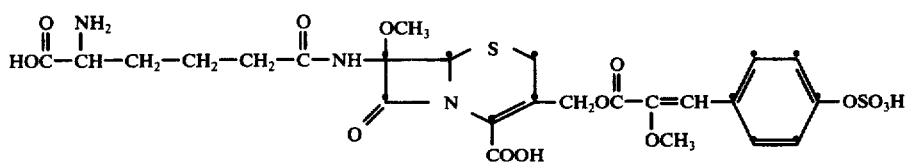

Ic

This compound has a greater resistance to cephalosporinases than cephalothin and is characterized by a low order of toxicity in mice. In addition it is more resistant to enzymatic degradation than cephalosporin C and it is bactericidal. Given orally it protects against infections due to *Proteus vulgaris* and, when administered intraperitoneally, it is effective against a variety of gram-negative and gram-positive infections.

THE MICROORGANISMS

810A Cultures: The microorganism which produces Antibiotic 810A was originally isolated as a single colony from soil. This colony was passed onto a streak plate of the following composition:

| Medium A: | |
|---|---|
| Yeast Extract | 10.0 g. |
| Dextrose | 10.0 g. |
| Agar | 20.0 g. |
| Distilled Water | 1000.0 ml. |

After several days of growth the microorganism produced the Antibiotic 810A. This antibiotic was then reproduced in shake flasks and differentiated from known antibiotics on the basis of various biological and chemical studies. Comparison of this data with that obtained via other known antibiotics established 810A as a new entity.

810A Taxonomy and Morphology: The microorganism (Culture MA-2837) which produces Antibiotic 810A has been identified as *Streptomyces griseus.* The taxonomy employed in this determination is described in "Bergey's Manual of Determinative Bacteriology", Seventh Edition; and in "The Actinomycetes", Vol. 2, by S.A. Waksman (1961). Using that procedure the culture was found to be a strain of *Streptomyces griseus* which closely resembles *Streptomyces griseinus* in description, melanin production and carbon utilization as described in Waksman and in the "International Journal of Systematic Bacteriology", Vol. 18: page 236 (1968). However, in both Waksman and in the "International Journal of Systematic Bacteriology", *Streptomyces griseinus* is narrowly defined as the "grisein-producing strain of *Streptomyces griseus*" or as "producing grisein or grisein-like substances". *Streptomyces griseus* (MA-2837) is a strain that differs from the classic description in Bergey and in Waksman inasmuch as it possesses an aerial mycelium which is predominantly tannish yellow and greenish yellow on some media and with a slightly different carbon utilization pattern. Waksman, on pages 111 and 133 of "The Actinomycetes" describes that *Streptomyces griseus* series as one which encompasses many related species and strains, as characterized by colorless to olive-buff substrate growth, aerial mycelium that is yellowish with a greenish tint, or greenish-grey or sear or grass-green to grey, melanin negative, sphorophores straight or flexuous and produced in tufts, spores oval. The following Tables compare the characteristics of the culture which produces Antibiotic 810A and the *Streptomyces griseus* and *Streptomyces griseinus* cultures.

The characterization of the parent isolate MA-2837 as compared with *Streptomyces griseus* described in Bergey[1] and Waksman[2] and, also, the characterization of MA-2837 as compared with *Streptomyces griseinus* as described in Waksman[2], are set forth in Tables I and Ia, infra.

TABLE I

COMPARISON OF CULTURAL CHARACTERISTICS OF MA-2837 CULTURE

| MA-2837 | *Streptomyces griseus* (Bergey[1]) | *Streptomyces griseus* (Waksman[2]) | *Streptomyces griscinus* (Waksman[2]) |
|---|---|---|---|
| Sporophores are monopodially branched forming tufts, with spore chains straight to slightly flexuous. Spores are spherical to oval, 0.9μ in diameter to 0.9×1.2μ, in chains of approximately 10-15 spores. Vegatative hyphae 0.9μ in width (Glycerol-asparagine agar-970X). | Aerial mycelium: Abundant, powdery, water green. Sporaphores produced in tufts. Spores spherical to ellipscidal, 0.8 by 0.8 to 1.7 microns. Vegetative growth: Colonies smooth or folded, colorless, later turning olive-buff. | Sporophores straight produced in tufts. Spores spherical to oval, 0.8 by 0.8 to 1.7μ; surface smooth. | Straight sporophores produced in clusters or tufts, without spirals. Spores rod-shaped, 1.0 to 1.8 by 0.8 to 1.0μ. |

[1]Bergey's "Manual of Determinative Bacteriology", Seventh Edition (1957).
[2]Waksman, S. A., "The Actinomycetes", Vol. 2 (1961).

TABLE Ia

COMPARISON OF CULTURAL CHARACTERISTICS OF MA-2837 CULTURE

| Medium | MA-2837 | *S. griseus* (Bergey) | *S. griseus* (Waksman) | *S. griseinus* (Waksman) |
|---|---|---|---|---|
| Tomato paste - oatmeal Agar | Vegetative Growth: Reverse-brown, flat, spreading<br>Aerial Mycelium: Center-tan to grayish-yellow; edge-tannish yellow<br>Soluble Pigment: Tan | | | |
| Glycerol-asparagine Agar | Vegetative Growth: Reverse-tan, flat, spreading<br>Aerial Mycelium: Powdery, tannish-yellow<br>Soluble Pigment: Light, tannish yellow | | | |
| Czapek-Dox Agar (Sucrose nitrate agar) | Vegetative Growth: Reverse-yellowish orange, flat, spreading<br>Aerial Mycelium: Powdery, tannish-yellow (several shades but predominantly tannish-yellow); growth light in center and heavier on edges<br>Soluble Pigment: Light, tannish yellow | | Growth thin, spreading, colorless, becoming olive-buff. Aerial mycelium thick, powdery, water green, pigment insoluble. | Substrate growth wrinkled, reverse cream-colored to brownish. Aerial mycelium white to cream-colored with light greenish tinge. No soluble pigment |
| Egg Albumin agar | Vegetative Growth: Reverse-grayish tan, flat, spreading<br>Aerial Mycelium: Tan-yellow with greenish cast, edge tannish yellow, light growth in center, heavier along edges.<br>Soluble Pigment: light tannish yellow | | | |
| Nutrient Agar | Vegetative Growth: Reverse-brownish yellow<br>Aerial Mycelium: Velvety, tannish yellow, edge tannish yellow<br>Soluble Pigment: Light brown | | Growth abundant, almost transparent, cream-colored. Aerial mycelium powdery, white to light gray. No soluble pigment. | |
| Agar | | | Abundant, cream-colored almost | |

TABLE Ia-continued
COMPARISON OF CULTURAL CHARACTERISTICS OF MA-2837 CULTURE

| Medium | MA-2837 | S. griseus (Bergey) | S. griseus (Waksman) | S. griseinus (Waksman) |
|---|---|---|---|---|
| | | transparent growth, aerial mycelium powdery, white to light grey. No soluble pigment. | | |
| Synthetic Agar | | Thin, spreading, colorless growth becoming olive-buff Aerial mycelium thick, powdery, water-green. | | |
| Gelatin Stab | Flaky cream-colored growth settling in bottom of tube. Complete liquefaction. | | Greenish yellow or cream-colored surface growth with brownish tinge. Rapid liquefaction. | Growth cream-colored with brownish tinge. Aerial mycelium absent or scant, white. Rapid liquefaction. |
| Nutrient Gelatin Agar | Vegetative Growth: Cream Aerial Mycelium: Pale, tannish yellow Soluble Pigment: None Liquefaction of gelatin-good. | | | |
| Litmus Milk | Partial ring Vegetative Growth: Brownish Aerial Mycelium: Slight, whitish Peptonization, becoming alkaline | | Cream-colored ring; coagulation with rapid peptoniaztion, becoming alkaline. | Growth cream-colored. Coagulation and petonization. |
| Skim Milk | Partial ring Vegetative Growth: Brownish Aerial Mycelium: None Soluble Pigment: Light brown Petonization, becoming alkaline | | | |
| Skim Milk Agar | Vegetative Growth: Cream, flat, spreading Aerial Mycelium: Sparse, yellowish white to cream Soluble Pigment: Very light brown Hydrolysis of casein | | | |
| Glucose Agar | | | Growth elevated in center, radiate, cream-colored to orange, erose margin | |
| Glucose Broth | | Abundant, yellowish pellicle with greenish tinge, much folded | | |
| Starch Agar | | Thin, spreading transparent growth Starch is hydrolyzed. | Growth thin, spreading, transparent, hydrolysis strong | Colorless to cream-colored growth Aerial mycelium grayish-olive. Hydrolysis rapid |
| Nutrient Starch Agar | Vegetative Growth: Cream Aerial Mycelium: Pale tannish yellow Soluble Pigment: None Hydrolysis good | | | |
| Potato Plug | Vegetative Growth: Light brown Aerial Mycelium: Moderate, tan Slight browning of potato. | Yellowish, wrinkled growth covered with white, powdery aerial mycelium. | Growth wrinkled, yellowish to brownish, covered with white, powdery aerial mycelium. | Growth wrinkled, yellowish-white. Aerial Mycelium grayish white with olive tinge. |
| Calcium Malate Agar | Vegetative Growth: Flat, spreading, translucent and colorless at edges, opaque and cream-colored in center. Aerial Mycelium: Moderate, cream to yellow, edges tannish yellow | | Green or yellow soluble pigment produced on calcium malate and succinate media. | No soluble pigments on calcium malate or succinate media. |

TABLE Ia-continued
COMPARISON OF CULTURAL CHARACTERISTICS OF MA-2837 CULTURE

| Medium | MA-2837 | S. griseus (Bergey) | S. griseus (Waksman) | S. griseinus (Waksman) |
|---|---|---|---|---|
| | Soluble Pigment: None | | | |
| Nutrient Tyrosine Agar | Vegetative Growth: Flat spreading, cream-colored Aerial Mycelium: Yellowish tan with greenish cast, edges tannish yellow Soluble Pigment: Very light brown Tyrosine crystals decomposed. | | Dark pigment often produced | No pigment produced |
| Peptone-iron-yeast Extract Agar | Vegetative Growth: Cream-colored Aerial Mycelium: None Soluble Pigment: None Melanin negative | | | |
| Production of $H_2S$ | Negative | | Negative | Negative |
| Loeffler's Blood Serum Slants | Vegetative Growth: Tan Aerial Mycelium: Slight, yellowish Soluble Pigment: Brownish Complete liquefaction. | | | |
| Temperature Range (yeast extract-dextrose-salts agar slants) | 28° C - good growth 37° C - good growth 50° C - no growth | Optimum temperature 37° C. | | |
| Microaerophilic Growth (yeast extract-dextrose-salts stab-40 mm depth) | Good growth covering surface and along entire stab line. | Aerobic | | |
| Reduction of nitrates to nitrites | Negative | Positive | Positive | Positive |

These observations were made after 3 weeks incubation at 28° C. except where otherwise noted. The pH of the media used in these studies was approximately neutral, that is, 6.8 to 7.2. The physiological tests were run at the end of 7 and 22 days. The colors used in the description are in accordance with the definitions of the "Color Harmony Manual", Fourth Edition, 1958; Container Corporation of America.

810A Carbohydrate Utilization: The *Streptomyces griseus* culture (MA-2837) was also tested for its ability to utilize or assimilate various carbohydrates by growing the microorganism in basal synthetic medium (T. G. Pridham and D. Gottlieb, Journal of Bacteriology, Vol. 56: page 107 (1948) containing 1% of the carbohydrate at 28° C. for 3 weeks. Table II infra, indicates the utilization or assimilation of these carbohydrate sources by the *Streptomyces griseus* culture (MA-2837). The explanation of the symbols in Table II are as follows: + indicates good growth, ± indicates poor growth, and — indicates no growth on the particular carbohydrate.

TABLE II

| Carbohydrate | MA-2837 Culture | Carbohydrate | MA-2837 Culture |
|---|---|---|---|
| Glucose | + | Lactose | ± |
| Arabinose | + | Inositol | ± |
| Mylose | + | Sucrose | ± |
| Maltose | + | Rhamnose | ± |
| Mannose | + | Raffinose | ± |
| Fructose | — | Cellulose | — |
| Mannitol | — | | |

The characteristics described in Tables I, Ia and II were used to reduce the *Streptomyces griseus* culture (MA-2837) to a species classification via the keys described in "Bergey's Manual of Determinative Bacteriology", Seventh Edition, pages 694–829 (1957) and in "The Actinomycetes", Vol. 2: pages 61–292 (1961). A comparison of the culture (MA-2837) with known species shows that it is similar to *Streptomyces griseus*. There are morphological differences as, for example, in the color of the aerial mycelium which, in *Streptomyces griseus*, is predominantly tannish yellow and greenish yellow but, in view of the significant number of similarities and the only minor differences there is no justification for a new species name. As a result, the microorganism (MA-2837) which produces Antibiotic 810A has been identified as a strain of *Streptomyces griseus*.

In addition to the foregoing culture (MA-2837), 25 additional cultures have been identified as producers of the Antibiotic 810A. These include: three cultures of *Streptomyces griseus*, eleven cultures of *Streptomyces viridochromogenes*, five cultures of *Streptomyces fimbriatus*, three cultures of *Streptomyces halstedii*, one culture of *Streptomyces rochei*, one culture of *Streptomyces cinnamonensis* and one culture of *Streptomyces chartreusis*. These strains of Streptomyces are identified as cultures MA-4160, MA-4174, MA-4171, MA-4177, MA-4178, MA-4180, MA-4164, MA-4165, MA-4166, MA-4167, MA-2892, MA-3265, MA-4162, MA-4163, MA-4159, MA-4169, MA-4170, MA-4179, MA-4161, MA-4168, MA-4175, MA-4181, MA-2938, MA-4176 and MA-4173 in the culture collection of Merck & Co., Inc., Rahway, New Jersey. These cultures have been placed on permanent deposit with the culture collection of the Northern Utilization Research and Development Branch of the U.S. Department of Agriculture at Peoria, Illinois.

The assigned NRRL culture numbers are as follows:

| Streptomyces griseus: | | |
|---|---|---|
| MA-4160 | NRRL | 3951 |
| MA-4174 | NRRL | 3953 |
| MA-4171 | NRRL | 3952 |
| Streptomyces viridochromogenes: | | |
| MA-4177 | NRRL | 3970 |
| MA-4178 | NRRL | 3971 |
| MA-4180 | NRRL | 3972 |
| MA-4164 | NRRL | 3966 |
| MA-4165 | NRRL | 3967 |
| MA-4166 | NRRL | 3968 |
| MA-4167 | NRRL | 3969 |
| MA-2892 | NRRL | 3962 |
| MA-3265 | NRRL | 3963 |
| MA-4162 | NRRL | 3964 |
| MA-4163 | NRRL | 3965 |
| Streptomyces fimbriatus: | | |
| MA-4159 | NRRL | 3954 |
| MA-4169 | NRRL | 3956 |
| MA-4170 | NRRL | 3957 |
| MA-4179 | NRRL | 3958 |
| MA-4161 | NRRL | 3955 |
| Streptomyces halstedii: | | |
| MA-4168 | NRRL | 3959 |
| MA-4175 | NRRL | 3960 |
| MA-4181 | NRRL | 3961 |
| Streptomyces rechei: | | |
| MA-2938 | NRRL | 3973 |
| Streptomyces cinnamonensis: | | |
| MA-4176 | NRRL | 3974 |
| Streptomyces chartreusis: | | |
| MA-4173 | NRRL | 3975 |

The characterization of the aforementioned isolates for comparison with *Streptomyces griseus, Streptomyces viridochromogenes, Streptomyces fimbriatus, Streptomyces halstedii, Streptomyces rochei, Streptomyces cinnamonensis* and *Streptomyces chartreusis* are set forth below in Tables IIa–IIe.

TABLE IIa

CULTURAL CHARACTERISTICS OF STRAINS OF *STREPTOMYCES GRISEUS* PRODUCING ANTIBIOTIC 810A

| Medium | MA-4160 | MA-4174 | MA-4171 |
|---|---|---|---|
| Morphology | Sporophores form tufts with spore chains straight to slightly flexuous. Spores are spherical to oval - 0.9µ dia. to 0.9µ × 1.2µ - in chains of approximately 10-15 spores. | | |
| Tomato Paste - Oatmeal Agar | —— Vegetative Growth: Good, flat, spreading, tan —— | | |
| | Aerial Mycelium: Powdery; tan with greenish cast | Aerial Mycelium: Powdery; tan with strong green overtone | Aerial Mycelium: Powdery; tan with strong green overtone |
| | —— Soluble Pigment: Light brown —— | | |
| Glycerol-asparagine Agar | —— Vegetative Growth: Good, flat, tan —— | | |
| | Aerial Mycelium: Powdery, tan with greenish cast and vectors of gray-green | | |
| | —— Soluble Pigment: Light brown —— | | |
| Czapek-Dox Agar | ——Vegetative Growth: Flat, spreading transparent —— | | |
| | Aerial Mycelium: Moderate; tan | Aerial Mycelium: Moderate; tan | Aerial Mycelium: Moderate; grayish |
| | Soluble Pigment: Light brown | Soluble Pigment: Light brown | Soluble Pigment: None |
| Yeast Extract - Dextrose + Salts Agar | —— Vegetative Growth: Flat, spreading, tan —— | | |
| | —— Aerial Mycelium: Good; powdery, beige —— | | |
| | —— Soluble Pigment: Light brown —— | | |
| Soluble Pigment on Peptone-Iron-Yeast Extract Agar | None | None | None |

TABLE IIb

| Medium | MA-2892 | MA-3265 | MA-4162 | MA-4163 |
|---|---|---|---|---|
| Czapek-Dox Agar | Vegetative Growth: Dark brown | Vegetative Growth: Dark brown | Vegetative Growth: Dark brown | Vegetative Growth: tan |
| | Aerial Mycelium: Very scant | Aerial Mycelium: Light gray & white | Aerial Mycelium: Very scant | Aerial Mycelium: Very scant |
| | Soluble Pigment: Dark brown | Soluble Pigment: Light brown | Soluble Pigment: Light brown | Soluble Pigment: Light brown |
| Yeast Extract-Dextrose Agar | Vegetative Growth: Dark brown | Vegetative Growth: Reverse brown | Vegetative Growth: Dark brown | Vegetative Growth: Dark brown |
| | Aerial Mycelium: Very scant | Aerial Mycelium: Light gray | Aerial Mycelium: Very scant | Aerial Mycelium: Very scant |
| | Soluble Pigment: Light brown | Soluble Pigment: None | Soluble Pigment: Light brown | Soluble Pigment: Light brown |
| Soluble Pigment on Peptone-Iron-Yeast Extract Agar | —— Dark brown —— | | | |

| Medium | MA-4164 | MA-4165 | MA-4166 | MA-4167 |
|---|---|---|---|---|
| Morphology | Sporophores are short, compact spirals occurring as side branches on aerial hyphae. Spores are spherical to oval - 0.9 to 1.2 diameter and 0.9 - 1.2 × 1.2 - 1.7 - in chains of approximately 10 - 15 spores. | | | |
| Tomato Paste-Oatmeal Agar | —— Vegetative Growth: Reverse dark brown —— | | | |
| | Aerial Mycelium: Velvety; blue-gray & cream | Aerial Mycelium: Velvety; medium gray & cream | Aerial Mycelium: Velvety; medium gray & cream | Aerial Mycelium: Velvety; dark gray & cream |
| | —— Soluble Pigment: Light brown —— | | | |
| Glycerol-aspara- | Vegetative Growth: | Vegetative Growth: | Vegetative Growth: | Vegetative Growth: |

TABLE IIb-continued

| gine Agar | Reverse dark brown<br>Aerial Mycelium:<br>Dark gray & cream | Reverse dark brown<br>Aerial Mycelium:<br>Medium gray & cream | Dark gray<br>Aerial Mycelium:<br>Scant-greyish | Reverse tan<br>Aerial Mycelium:<br>Light gray & cream |
|---|---|---|---|---|
| | | Soluble Pigment: Light brown | | |
| Czapek-Dox Agar | Vegetative Growth:<br>Brown<br>Aerial Mycelium:<br>Very scant | Vegetative Growth:<br>Reverse brown<br>Aerial Mycelium:<br>Light gray & cream | Vegetative Growth:<br>Brown<br>Aerial Mycelium:<br>Very scant | Vegetative Growth:<br>Tan<br>Aerial Mycelium:<br>Very scant |
| | Soluble Pigment:<br>Brown | Soluble Pigment:<br>Light brown | Soluble Pigment:<br>Brown | Soluble Pigment:<br>Light brown |
| Yeast Extract-Dextrose Agar | Vegetative Growth: Dark brown<br>Aerial Mycelium: Very scant<br>Soluble Pigment: Light brown | | | |
| Soluble Pigment on Peptone-Iron-Yeast Extract Agar | Dark brown | | | |

| Medium | MA-4177 | MA-4178 | MA-4180 |
|---|---|---|---|
| Morphology | Sporophores are short, compact spirals occurring as side branches on aerial hyphae. Spores are spherical to oval - 0.9 to 1.2μ diameter and 0.9 - 1.2 × 1.2 -1.7μ - in chains of approximately 10 - 15 spores. | | |
| Tomato Paste-Oatmeal Agar | Vegetative Growth:<br>Reverse tan<br>Aerial Mycelium:<br>Velvety; dark gray & white | Vegetative Growth:<br>Reverse brown<br>Aerial Mycelium:<br>Velvety; dark gray | Vegetative Growth:<br>Reverse brown<br>Aerial Mycelium:<br>Velvety; dark gray & cream |
| | Soluble Pigment: Light brown | | |
| Glycerol-asparagine Agar | Vegetative Growth:<br>Reverse brown<br>Aerial Mycelium:<br>Dark gray | Vegetative Growth:<br>Reverse dark brown<br>Aerial Mycelium:<br>Dark gray | Vegetative Growth:<br>Reverse dark brown<br>Aerial Mycelium:<br>Mixture of light & dark gray |
| | Soluble Pigment: Light brown | | |
| Czapek-Dox Agar | Vegetative Growth:<br>Tan | Vegetative Growth:<br>Dark brown | Vegetative Growth:<br>Tan |
| | Aerial Mycelium: Very scant | | |
| | Soluble Pigment: Light brown | | |
| Yeast Extract-Dextrose Agar | Vegetative Growth:<br>Dark brown<br>Aerial Mycelium:<br>Scant-grayish | Vegetative Growth:<br>brown<br>Aerial Mycelium:<br>Very scant | Vegetative Growth:<br>Brown<br>Aerial Mycelium:<br>Very scant |
| | Soluble Pigment: Light brown | | |
| Soluble Pigment on Peptone-Iron-Yeast Extract Agar | Dark brown | | |

TABLE IIc

CULTURAL CHARACTERISTICS OF STRAINS OF *STREPTOMYCES FIMBRIATUS* PRODUCING ANTIBIOTIC 810A

| Medium | MA-4159 | MA-4169 | MA-4170 | MA-4179 | MA-4161 |
|---|---|---|---|---|---|
| Morphology | Sporophores are short, compact spirals and some loops, occurring as side branches on aerial hyphae. Spores are spherical to oval - 0.9μ diameter and 0.9 × 1.2μ - chains of approximately 10 - 15 spores. | | | | Sporophores are short hooks & loops, occurring as side branches on aerial mycelium. Spores are in chains of less than 10 spores - spherical to oval, 0.9μ diameter & 0.9 × 1.2μ |
| Tomato Paste-Oatmeal Agar | Vegetative Growth:<br>Reverse tan<br>Aerial Mycelium:<br>Moderate; light gray | Vegetative Growth:<br>Reverse tan<br>Aerial Mycelium:<br>Moderate; light gray | Vegetative Growth:<br>Reverse tan<br>Aerial Mycelium:<br>Moderate; light gray & cream | Vegetative Growth:<br>Reverse tan<br>Aerial Mycelium:<br>Sparse, grayish | Vegetative Growth:<br>Tan<br>Aerial Mycelium:<br>Scant; grayish |
| | Soluble Pigment: Light brown | | | | |
| Glycerol-asparagine Agar | Vegetative Growth:<br>Dark brownish-gray | Vegetative Growth:<br>Dark brownish-gray | Vegetative Growth:<br>Dark brownish-gray | Vegetative Growth:<br>Dark brownish-gray | Vegetative Growth:<br>Reverse tan with reddish tan vector |
| Czapek-Dox Agar | Vegetative Growth:<br>Dark brownish-gray<br>Aerial Mycelium:<br>Very scant<br>Soluble Pigment:<br>Brown | Vegetative Growth:<br>Dark brownish-gray<br>Aerial Mycelium:<br>Moderate; gray<br>Soluble Pigment:<br>Brown | Vegetative Growth:<br>Dark brownish-gray<br>Aerial Mycelium:<br>Moderate; gray<br>Soluble Pigment:<br>Brown | Vegetative Growth:<br>Dark brownish-gray<br>Aerial Mycelium:<br>Very scant<br>Soluble Pigment:<br>Brown | Vegetative Growth:<br>Tan<br>Aerial Mycelium:<br>Very scant<br>Soluble Pigment:<br>Light brown |
| Yeast Extract Dextrose + Salts Agar | Vegetative Growth:<br>Dark brownish-gray | Vegetative Growth:<br>Dark brownish-gray | Vegetative Growth:<br>Dark brownish-gray | Vegetative Growth:<br>Dark brownish-gray | Vegetative Growth:<br>Brown |
| | Aerial Mycelium: Very scant | | | | |
| | Soluble Pigment: Brown | | | | |
| Soluble | | | | | |

TABLE IIc-continued
CULTURAL CHARACTERISTICS OF STRAINS OF *STREPTOMYCES FIMBRIATUS* PRODUCING ANTIBIOTIC 810A

| Medium | MA-4159 | MA-4169 | MA-4170 | MA-4179 | MA-4161 |
|---|---|---|---|---|---|
| Pigment on Peptone-Iron-Yeast Extract Agar | | | Dark brown | | |

TABLE IId
CULTURAL CHARACTERISTICS OF STRAINS OF *STREPTOMYCES HALSTEDII* PRODUCING ANTIBIOTIC 810A

| Medium | MA-4168 | MA-4175 | MA-4181 |
|---|---|---|---|
| Morphology | Sporophores are long, loose spirals occurring as side branches on aerial hyphae. Spores are spherical to oval - 0.9μ diameter and 0.9 × 1.2μ - in chains of more than 10 spores. | | |
| Tomato Paste-Oatmeal Agar | Vegetative Growth: Reverse brown  Aerial Mycelium: Powdery; dark grey | Vegetative Growth: Reverse tan  Aerial Mycelium: Dark grey & white; powdery  Soluble Pigment: None | Vegetative Growth: Reverse brown  Aerial Mycelium: Dark grey & white |
| Glycerol-asparagine Agar | Vegetative Growth: Reverse brown to dark brown  Aerial Mycelium: Powdery; dark grey and white | Vegetative Growth: Reverse greyish  Aerial Mycelium: Powdery, predominantly, dark grey mixed with light grey and white  Soluble Pigment: None | Vegetative Growth: Reverse greyish  Aerial Mycelium: Dark grey; powdery |
| Czapek-Dox Agar | Vegetative Growth: Cream  Aerial Mycelium: Greyish cream | Vegetative Growth: Reverse reddish brown  Aerial Mycelium: Greyish cream  Soluble Pigment: None | Vegetative Growth: Cream  Aerial Mycelium: Very scant |
| Yeast Extract Dextrose + Salts Agar | Vegetative Growth: Tan  Aerial Mycelium: Greyish; scant | Vegetative Growth: Tan  Aerial Mycelium: Scant; greyish  Soluble Pigment: None | Vegetative Growth: Brown  Aerial Mycelium: Scant; greyish |
| Soluble Pigment Peptone-Iron-Yeast Extract Agar | | None | |

TABLE IIe
CULTURAL CHARACTERISTICS OF *STREPTOMYCES* SPECIES PRODUCING ANTIBIOTIC 810A

| Medium | MA-2938 *Streptomyces rochei* | MA-4176 *Streptomyces cinnamonensis* | MA-4173 *Streptomyces chartreusis* |
|---|---|---|---|
| Morphology | Sporophores form compact spirals occurring as side chains of approximately 10 - 15 spores - spherical to oval, 0.9μ diameter & 9 × 1.2μ | Sporophores are hooks, loops, & a few loose spirals, occurring as side branches on aerial hyphae. Spores are in chains of more than 10 spores - spherical to oval, 0.9μ diameter & 0.9 × 1.2μ | Sporophores are compact spirals, occurring as side branches on aerial hyphae. spores are in chains of more than 10 spores - spherical to oval, 0.9 - 1.2μ diameter & 0.9 - 1.2 × 1.2 - 1.7μ |
| Tomato Paste-Oatmeal Agar | Vegetative Growth: Reverse reddish-brown  Aerial Mycelium: Medium gray  Soluble Pigment: None | Vegetative Growth: Tan  Aerial Mycelium: Beige with pink tint; velvety  Soluble Pigment: Brown | Vegetative Growth: Light brown with vectors of orange-brown  Aerial Mycelium: Powdery; dark gray with blue-green tint  Soluble Pigment: Brown |
| Glycerol-asparagine Agar | Vegetative Growth: Reverse reddish-brown  Aerial Mycelium: Medium gray  Soluble Pigment: None | Vegetative Growth: Reverse dark reddish-brown  Aerial Mycelium: Beige with pink tint  Soluble Pigment: Brown | Vegetative Growth: Brown  Aerial Mycelium: Very scant  Soluble Pigment: Light brown |
| Czapek-Dox Agar | Vegetative Growth: Reddish brown  Aerial Mycelium: Very scant  Soluble Pigment: None | Vegetative Growth: Reverse dark brown  Aerial Mycelium: Moderate; beige with pink tint  Soluble Pigment: Brown | Vegetative Growth: Orange-brown  Aerial Mycelium: Very scant  Soluble Pigment: Light brown |
| Yeast Extract Dextrose + Salts Agar | Vegetative Growth: Tan  Aerial Mycelium: Grayish  Soluble Pigment: Light brown | Vegetative Growth: Brown  Aerial Mycelium: Sparse creamish-white  Soluble Pigment: Light brown | Vegetative Growth: Brown  Aerial Mycelium: Very scant  Soluble Pigment: Brown |
| Soluble Pigment on Peptone-Iron-Yeast Extract Agar | None | Dark Brown | Dark Brown |

The foregoing description of the microorganisms producing Antibiotic 810A is simply illustrative of the type of strains which can be used and it should be understood that this invention is not limited to an organism meeting these particular descriptions. This invention includes the use of other microorganisms including strains of actinomycetes isolated from nature or obtained by mutation as, for example, those obtained by natural selection or those produced by mutating agents as, for example, X-ray irradiation, ultraviolet irradiation, nitrogen mustards and the like which, under suitable conditions will yield an identical antibiotic.

842A Culture: The microorganism which produces Antibiotic 842A is a previously unknown strain of actinomycete. The original isolate was obtained as a single colony from soil on an agar slant and grown in a medium having the following composition:

| Medium B: | |
|---|---|
| Yeast Extract | 10.0 g. |
| Glucose | 10.0 g. |
| *Phosphate Buffer | 2.0 ml. |
| $MgSO_4 . 7H_2O$ | 0.05 g. |
| Distilled Water | 1000.0 ml. |
| pH 6.5 | |
| *Phosphate Buffer | |
| $KH_2PO_4$ | 91.0 g. |
| $Na_2HPO_4$ | 95.0 g. |
| Distilled Water | 1000.0 ml. |

After several days of growth it was found that no sporulation could be detected. The microorganism produced an antibiotic which was differentiated from known antibiotics on the basis of its profile in various biological and chemical studies. Comparison of this data with that obtained via other known antibiotics established 842A as a new entity.

842A Taxonomy: The microorganism (Culture MA-2908) which produces 842A has been identified as a new species of actinomycetes. The taxonomy employed in this determination is described in "Bergey's Manual of Determinative Bacteriology", Seventh edition; and in "The Actinemycetes", Vol. 2, "Classification, Identification and Description of Genera and Species", S. A. Waksman (1961). Using that procedure the culture was found to belong to the genus Streptomyces and it possesses many of the attributes of the known species *Streptomyces fradiae*. Biochemically it is an essentially perfect match with the latter. Morphologically, however, there are important differences. For example, the color of the aerial mycelium of *S. fradiae* is a seashell pink whereas the culture MA-2908 is usually cream colored. Also, the vegetative growth in the MA-2908 culture shows pigment differences on the various media employed, and, as stated below, no sporulation was detected on standard taxonomic media. On the basis of these differences, the culture was assigned a new species name: *Streptomyces lactamdurans*. Table III, infra, describes the biochemical attributes of the *Streptomyces lactamdurans* species and those of the known *Streptomyces fradiae*. All of the readings in Table III were taken after 3 weeks incubation at 28° C. except where otherwise noted. The pH of the media used in these studies was approximately neutral, namely, 6.8 to 7.2. The physiological tests were run at the end of 7 and 21 days.

TABLE III

| | 842A Biochemical Comparison | |
|---|---|---|
| Test | Streptomyces lactamdurans | Streptomyces fradiae |
| aerial mycelium | straight, some branching | straight, branching-filaments |
| conidia | none detected | rod-shaped |
| soluble pigment | none | none |
| optimum temperature | 28° C. | 25° C. |
| invertase | negative | negative |
| reduction of nitrate | negative | negative |
| gelatin liquefaction | positive | positive |
| cellulose utilization | negative | negative |
| litmus milk | alkaline; peptonization | alkaline; peptonization |

842A Morphology: Sporophores were not detected when the culture was grown on the media listed in the description of culture characteristics even though repeated observations were made up to 8 weeks. However, stained impression slides showed long filaments, many segmented into sub-units of various sizes, generally rod shaped and approximately 0.9 by 1.7 microns in size.

Tomato-Paste-Oatmeal Agar
  Vegetative growth—reverse—orange; flat, dry appearing, wrinkled
  Aerial Mycelium—sparse, cream
  No soluble pigment Czapek-Dox Agar
  Vegetative—flat, deep cream
  Aerial Mycelium—powdery, creamish white
  No soluble pigment Glycerol-Asparagine Agar
  Vegetative growth—flat, reverse—golden yellow to orange
  Aerial Mycelium—powdery, cream with pale peach tones
  Soluble pigment—pale amber Egg Albumin Agar
  Vegetative growth—flat, cream to yellow
  Aerial Mycelium—powdery, cream
  No soluble pigment Calcium Malate Agar
  Vegetative growth—flat; reverse—yellow edged with orange
  Aerial Mycelium—powdery, white to cream edged with peach
  No soluble pigment Nutrient Tyrosine Agar
  Vegetative growth—flat, tan to orange Aerial Mycelium—sparse, cream with white
No soluble pigment
Tyrosine crystals decomposed Molasses—Yeast Hydrolysate Agar
  Vegetative growth—flat; reverse—orange
  Aerial Mycelium—powdery, creamish white
  No soluble pigment Nutrient Agar
  Vegetative growth—flat, golden yellow
  Aerial Mycelium—powdery, cream
  No soluble pigment Litmus Milk
  Sparse growth ring—tan vegetative growth—no aerial mycelium
  Peptonization: alkaline reaction;
  pH 7.3–7.4 (Control pH—6.7)

Skim Milk
  Sparse growth ring—tan to orange
  Vegetative growth—no aerial mycelium
  Light tan soluble pigment
  Peptonization—alkaline reaction
  pH 7.2 (Control pH—6.6)

Skim Milk Agar
  Vegetative growth—flat, orange
  Aerial Mycelium—moderate, cream to pale coral
  Light tan soluble pigment
  Hydrolysis of casein Gelatin Stab
  Sparse cream to orange colored flaky vegetative growth suspended throughout tube
  No soluble pigment
  Complete liquefaction Nutrient Gelatin Agar
  Vegetative growth—flat, orange
  Aerial Mycelium—sparse, powdery, cream
  No soluble pigment
  Liquefaction of gelatin Nutrient Starch Agar
  Vegetative growth—flat, orange
  Aerial Mycelium—sparse, powdery, pinkish cream
  No soluble pigment
  Moderate hydrolysis of starch Synthetic Starch Agar
  Vegetative growth—flat; reverse—cream edged with orange
  Aerial Mycelium—powdery, white edged with peach
  No soluble pigment
  Moderate hydrolysis of starch Loeffler's Blood Serum Agar
  Vegetative growth—cream colored to orange
  Aerial Mycelium—none
  No soluble pigment
  No liquefaction Peptone-Iron-Yeast Extract Agar
  Vegetative growth—cream
  Aerial—sparse-whitish
  No soluble pigment Microaerophilic Growth
  (Yeast extract-dextrose stab—40 mm. depth of stab.)
  Good surface growth and along upper ¼ of stab line.

Temperature—Yeast extract-dextrose slants
  Good growth at 28° C.
  Sparse growth at 37° C.
  No growth at 50° C.

Yeast Extract—Dextrose Agar
  Vegetative growth—flat, golden yellow
  Aerial Mycelium—powdery, cream to pale flesh pink
  No soluble pigment Potato plug
  Vegetative growth—dry, flat, cream to orange
  Aerial Mycelium—sparse, creamish
  No soluble pigment Reduction of Nitrates to Nitrites—Negative All readings were taken after 3 weeks incubation at 28° C. except where noted otherwise. Physiological tests were run at 7 and 21 days.

The morphological differences between *Streptomyces lactamdurans* and *Streptomyces fradiae* are set forth in Table IV, infra. The observations were made on the media indicated in Table IV at growth intervals of 1 week, 3 weeks and 8 weeks. The aerial mycelium of *S. lactamdurans* is short and straight with little branching. It appears to be about the same size as the vegetative mycelium, i.e., 0.9 micrometer in width. It is light, powdery and scrapes off easily. The vegetative mycelium is gram-positive; it is not acid-fast. It clings to and in some media is imbedded in the agar. There is some fragmentation into rods in shake-flask growth but this is not extensive. Vegetative mycelium from shaker and stationary flasks (seed medium 4 to 6 days, 28° C.) showed some "buds" and short, thickened, almost club-shaped segments on mycelium but these were not numerous. All of the readings in Table IV were taken after 3 weeks incubation at 28° C. except where otherwise noted. The pH of the media used in these studies was approximately neutral, that is, 6.8 to 7.2. The physiological tests were run at the end of 7 and 21 days. The colors used in the description are in accordance with the definitions of the "Color Harmony Manual", Fourth Edition, 1958; Container Corporation of America.

TABLE IV

| Medium | 842A; Morphological Comparison of *Streptomyces lactamdurans* and *Streptomyces fradie* | | | |
| --- | --- | --- | --- | --- |
| | *Streptomyces lactamdurans* | | *Streptomyces fradiae* | |
| Czapek-Dox Agar | Vegetative Growth: Aerial Mycelium: No Soluble Pigment | Flat, deep cream Powdery, creamish white | Vegetative Growth: Aerial Mycelium: | Colorless Seashell pink |
| Nutrient Agar | Vegetative Growth: Aerial Mycelium: No Soluble Pigment | Flat, cream to golden yellow Powdery, cream | Vegetative Growth: | Orange-yellow |

TABLE IV-continued
842A; Morphological Comparison of *Streptomyces lactamdurans* and *Streptomyces fradie*

| Medium | Streptomyces lactamdurans | | Streptomyces fradiae | |
| --- | --- | --- | --- | --- |
| Glycerol-Asparagine Agar | Vegetative Growth: | Flat, reverse - golden yellow to orange | Vegetative Growth: | Buff-colored |
| | Aerial Mycelium: | Powdery, cream with pale peach tones | | |
| | Soluble Pigment: | Pale amber | | |
| Yeast Extract - Dextrose Agar | Vegetative Growth: Aerial Mycelium: | Flat, golden yellow Powdery, cream to pale flesh pink | Vegetative Growth: | Buff-colored |
| | No Soluble Pigment | | | |
| Synthetic Starch Agar | Vegetative Growth: | Flat, reverse - cream edged with orange | Vegetative Growth: | Colorless |
| | Aerial Mycelium: | Powdery, white edged with peach | Aerial Mycelium: | Seashell pink |
| | No Soluble Pigment Moderate Hydrolysis of Starch | | | |
| Potato Plug | Vegetative Growth: | Dry, flat, cream to orange | Vegetative Growth: | Orange |
| | Aerial Mycelium: No Soluble Pigment | Sparse, creamish | | |
| Gelatin Stab | Vegetative Growth: | Sparse cream to orange flakes suspended throughout the tube | Vegetative Growth: | Cream to brown |
| | Aerial Mycelium: No Soluble Pigment | | | |
| Complete Liquefaction | | | | |
| Litmus Milk | Vegetative Growth: Aerial Mycelium: Peptonization, alkaline reaction; pH 7.3 - 7.4 (Control pH: 6.7) | Tan; sparse growth ring None | Vegetative Growth: | Cream colored |

842A Carbohydrate Utilization: The *Streptomyces lactamdurans* culture (MA-2908) was also tested for its ability to utilize or assimilate various carbohydrates by growing the microorganism in a basal synthetic medium (T. G. Pridham and D. Gottlieb; Journal of Bacteriology, Vol. 56: page 107 (1948)) which contains 1% of the carbohydrate at 28° C. for 3 weeks. Table V indicates the utilization or assimilation of these carbohydrate sources by the *Streptomyces lactamdurans* culture (MA-2908). The explanation of the symbols in Table V are as follows: + indicates good growth, ± indicates poor growth and - indicates no growth on the particular carbohydrate.

TABLE V

| Carbohydrate | MA-2908 Culture | Carbohydrate | MA-2908 Culture |
| --- | --- | --- | --- |
| Glucose | + | Rhamnose | − |
| Arabinose | + | Cellulose | − |
| Maltose | + | Fructose | ± |
| Raffinose | + | Inositol | − |
| Sucrose | − | Acetate | ± |
| Xylose | + | Citrate | ± |
| Mannitol | + | Paraffin | − |
| Lactose | − | Glycerol | ± |
| Mannose | − | | |

The characteristics described in Tables III, IV and V were used to reduce the *Streptomyces lactamdurans* culture (MA-2908) to a species classification via the keys described in "Bergey's Manual of Determinative Bacteriology", Seventh Edition, pages 694–829 (1957) and in "The Actinomycetes", Vol. 2: pages 61–292 (1961). A comparison of the detailed characteristics of the *Streptomyces lactamdurans* culture with known species showed that the culture is biochemically similar to *Streptomyces fradiae*. However, as indicated above, there are important morphological differences as, for example, in the color of the aerial mycelium of *S. fradiae* which is seashell pink as compared to the cream color of the culture. Also, the vegetative growth with *S. fradiae* shows pigment differences on the various media and no sporulation was detected with the culture MA-2908. On the basis of these differences and the characteristics described in the foregoing Tables the microorganism producing antibiotic 842A (MA-2908) was assigned the new species name *Streptomyces lactamdurans*.

The foregoing description of the microorganism which produces antibiotic 842A is simply illustrative of the type of strains of microorganisms which can be used and it should be understood that the present invention is not limited to organisms meeting these particular descriptions. This invention includes the use of other microorganisms, including strains of actinomycetes either isolated from nature or obtained by mutation as, for example, those obtained by natural selection of those produced by mutating agents, for example, X-ray irradiation, ultraviolet irradiation, nitrogen mustards and the like which, under suitable conditions, will afford the 842A product.

IN VITRO AND IN VIVO STUDIES

Antibiotic 810A; In vitro: The in vitro biological characterization of Antibiotic 810A was established by the disc-plate agar diffusion method. These tests were performed by placing 7 mm. discs, wet with the antibiotic solution, on the surface of petri plates poured with 5 ml. of Difco Nutrient Agar and 0.2% Yeast Extract seeded with 5 or 10 ml. of inoculum per 150 ml. of medium and incubated at 25° or 37° C. for 16 hours. The method and philosophy of these tests are described in the publication: "Cross Resistance Studies and Antibiotic Identification", Applied Microbiology, Vol. 6: pages 392–398 (1958). The following Tables VI, VII, and VIII set forth the results of these antibacterial and cross-resistance tests and indicate the test organisms used and the conditions employed.

TABLE VI

810A ANTIBACTERIAL SPECTRUM In Vitro Activity

| Test Organism | Test Conditions | | Inhibition Zone Diameter, mm* |
|---|---|---|---|
| | Inoculum** ml/150 ml | Incubation Temp. ° C. | 810A 5mg/ml |
| Escherichia coli | 5 | 25 | 15 |
| Bacillus species | 5 | 25 | 22 |
| Proteus vulgaris | 5 | 37 | 29 |
| Pseudomonas aeruginosa | 5 | 25 | 7 |
| Serratia marcescens | 5 | 25 | 7 |
| Staphylococcus aureus | 5 | 25 | 26 |
| Bacillus subtilis | 5 | 25 | 33 |
| Sarcina lutea | 5 | 25 | 26 |
| Staphylococcus aureus (Streptomycin-Streptothricin-resistant) | 5 | 37 | 19 |
| Streptococcus faecalis | 15 | 37 | 7 |
| Alcaligenes faecalis | 5 | 37 | 25 |
| Brucella bronchiseptica | 10 | 37 | 21 |
| Salmonella gallinarum | 10 | 25 | 15 |
| Vibrio porcolans | 10 | 27 | 36 |
| Xanthomonas vesicatoria | 5 | 25 | 15 |

*7 mm = disc size (no inhibition zone observed)
**Overnight culture diluted to a reading of 60 mµ on the Lumetron colorimeter.

TABLE VII

810A CROSS-RESISTANCE; In Vitro Study

| Escherichia coli-Strain** | Test Conditions | | Inhibition Zone Diameter, mm* |
|---|---|---|---|
| | Inoculum*** ml/150 ml | Incubation Temp. ° C. | 810A 5 mg/ml |
| Sensitive parent | 5 | 25 | 15 |
| Streptomycin-resistant | 5 | 25 | 13 |
| Streptothricin-resistant | 10 | 25 | 17 |
| OXAMYCIN-resistant | 10 | 25 | 10 |
| Pleocidin-resistant | 10 | 37 | 26 |
| Chloramphenicol-resistant | 10 | 25 | 7 |
| Chlortetracycline-resistant | 10 | 25 | 7 |
| Oxytetracycline-resistant | 10 | 25 | 7 |
| Neomycin-resistant | 10 | 37 | 20 |
| Tetracycline-resistant | 10 | 25 | 7 |
| Viomycin-resistant | 10 | 37 | 17 |
| Polymyxin-resistant | 10 | 25 | 13 |
| Grisein-resistant | 5 | 25 | 15 |

*7 mm = disc size (no inhibition zone observed)
**Tests performed versus a series of E. coli isolated from the same parent culture following exposure to the individual antibiotics
***Overnight culture diluted to a reading of 60 mµ on the Lumetron colorimeter.

TABLE VIII

810A SPECIAL EFFECTS SPECTRUM; In Vitro Study

| Eschericha coli W-MB-60 (with special addition noted) | Test Conditions | | Inhibition Zone Diameter, mm* |
|---|---|---|---|
| | Inoculum** ml/150 ml | Incubation Temp. ° C. | 810A 5 mg/ml |
| Control (no additions) | 5 | 25 | 13 |
| 0.1 M Phosphate Buffer - pH 5 | 5 | 25 | 13 |
| 0.1 M Phosphate Buffer - pH 7 | 5 | 25 | 16 |
| 0.1 M Phosphate Buffer - pH 9 | 5 | 25 | 18 |
| Human Blood Plasma 20% | 5 | 25 | 15 |
| Cation Exchange Resin (Dow ET 91-1%; agar concentration reduced to 1% for resin plate only) | 5 | 25 | 12 |

*7 mm disc size (no inhibition zone observed)
**Overnight culture diluted to a reading of 60 mµ on the Lumetron colorimeter.

Antibiotic 810A; In vivo: THe in vivo biological characterization indicates that 810A is a broad spectrum antibiotic which protects against infection with two species of Proteus, two of Salmonella, two strains of Escherichia coli, one of Klebsiella and three gram-positive organisms: *Staphylococcus aureus, Streptococcus pyogenes* and *Diplococcus pneumoniae.*

Methods: The method employed in this characterization is as follows: Female white Swiss mice, average weight 20-23 grams, were infected intraperitoneally with 3-20 times the number of organisms calculated to be lethal for 50% of the infected control animals (3-20 $LD_{50}$ doses). At the time of infection and again 6 hours later, therapy was given by the designated route. Controls of the virulence of the culture and the toxicity of the antibiotic for uninfected mice were included in the tests. Seven days after infection the test was considered complete and the amount of the antibiotic (I) that would be required to protect 50% of the infected and treated animals was calculated by the method of Knudsen and Curtis: J. Amer. Stat. Assoc. Vol. 42: page 282 (1947).

Results: The results of these tests are listed in Table IV, infra. This data indicates that the antibiotic 810A obtained from culture MA-2837 is a broad spectrum agent, protecting against both gram-positive and gram-negative organisms.

Although effective orally (p.o.) 810A is most effective via the subcutaneous (s.c.) or intraperitoneal (i.p.) route. The antibiotic mixture did not kill uninfected mice when two doses containing 1 mg. each of the product were administered intraperitoneally or when two doses of 18 mg. each were administered subcutaneously or orally.

TABLE IX

| Test Organism | 810A In Vitro Activity | |
|---|---|---|
| | Route of Therapy | $ED_{50}$ in Micrograms × Two Doses |
| Proteus vulgaris | i.p. | 33 |
| | s.c. | 500 |
| | p.o. | 12100 |
| Proteus mirabilis | i.p. | 200 |
| | p.c. | >5000 |
| Salmonella schottmuelleri | i.p. | 419 |
| | s.c. | 9000 |
| Escherichia coli | i.p. | 3750 |
| Escherichia coli | i.p. | 1330 |
| Klebsiella pneumoniae | i.p. | 2500 |
| Salmonella gallinarum | i.p. | 1670 |
| Salmonella pullorum | i.p. | 625 |
| Diplococcus pneumoniae | i.p. | 258 |
| Staphylococcus aureus | i.p. | 927 |
| Streptococcus pyogenes | i.p. | 625 |

Antibiotic 842A; In vitro: The in vitro biological characterization was established by the disc-plate agar diffusion method. These tests were performed by placing 7 mm. discs, wet with the antibiotic solution, on the surface of petri plates poured with 5 ml. of Difco Nutrient Agar and 0.2% Yeast Extract seeded with 5 or 10 ml. of standard cell suspension (OD = 0.22 at 660 mµ) per 150 ml. of medium and incubated at 25° or 37° C. for 16 hours as indicated. The method and philosophy of these tests are described in the publication: "Cross Resistance Studies and Antibiotic Identification", Applied Microbiology, Vol. 6: pages 392–398 (1958). The following Tables set forth the results of these antibacterial spectrum and cross-resistance tests, and indicate the test organisms used and the conditions employed.

The method employed in these studies is the same as described above with regard to the in vivo characterization of 810A. The results of these tests are described below in Table XIb:

TABLE X

842A ANTIBACTERIAL SPECTRUM; IN VITRO ACTIVITY

| Test Organism | Test Conditions | | INHIBITION ZONE DIAMETER, mm* | | |
|---|---|---|---|---|---|
| | Inoculum ml/150 ml | Incubation Temp. °C. | Crude 842κ (Ib) 8 mg/ml | Free Acid 166 µg/ml | Sodium Salt 192 µg/ml |
| *Escherichia coli* | 5 | 25 | 16 | 20 | 18 |
| *Bacillus sp.* | 5 | 25 | 7 | 8 | 7 |
| *Proteus vulgaris* | 5 | 37 | 21 | 22 | 24 |
| *Pseudomonas aeruginosa* | 5 | 25 | 7 | 7 | 7 |
| *Serrglia marcescena* | 5 | 25 | 7 | 7 | 7 |
| *Staphylococcus aureus* | 5 | 25 | 7 | 7 | 7 |
| *Bacillus subtilis* | 5 | 25 | 16 | 13 | 18 |
| *Sarcina lutea* | 5 | 25 | 9 | 10 | 9 |
| *Staphylococcus aureus* (Streptomycin-Streptothricin-resistant) | 5 | 37 | 7 | 11 | 10 |
| *Streptococcus faecalis* | 15 | 37 | 7 | 7 | 7 |
| *Alcaligenes faecalis* | 5 | 37 | 22 | 27 | 7 |
| *Brucella bronchiseptica* | 10 | 37 | 28 | 24 | 26 |
| *Salmonella gallinarum* | 10 | 25 | 20 | 21 | 25 |
| *Vibrio percolans* | 10 | 27 | 37 | 30 | 38 |
| *Xanthomonas vesicatoria* | 5 | 25 | 12 | 19 | 17 |

*7 mm = disc size (no inhibition zone observed)

TABLE XI

842A CROSS RESISTANCE; IN VITRO STUDY

| *Escherichia coli* - Strain** | Test Conditions | | INHIBITION ZONE DIAMETER, mm* | | |
|---|---|---|---|---|---|
| | Inoculum ml/150 ml | Incubation Temp. °C. | Crude 842A (Ib) 8 mg/ml | Free Acid 166 µg/ml | Sodium Salt 192 µg/ml |
| Sensitive parent | 5 | 25 | 16 | 20 | 18 |
| *Streptomycin*-resistant | 5 | 25 | 14 | 19 | 16 |
| *Streptothricin*-resistant | 10 | 25 | 13 | 14 | 18 |
| *OXMYCIN*-resistant | 10 | 25 | 13 | 13 | 17 |
| *Pleocidin*-resistant | 10 | 37 | 15 | 18 | 17 |
| *Chloramphenicol*-resistant | 10 | 25 | 13 | 17 | 16 |
| *Chlortetracycline*-resistant | 10 | 25 | 21 | 20 | 23 |
| *Oxytetracycline*-resistant | 10 | 25 | 20 | 23 | 24 |
| *Neomycin*-resistant | 10 | 37 | 18 | 17 | 17 |
| *Tetracycline*-resistant | 10 | 25 | 16 | 20 | 20 |
| *Viomycin*-resistant | 10 | 37 | 15 | 16 | 30 |
| *Polymyxin*-resistant | 10 | 25 | 23 | 21 | 7 |
| *Grisoin*-resistant | 5 | 25 | 18 | 21 | 16 |

**Tests performed versus a series of strains of *E. coli* isolated from the same parent culture following exposure to the individual antibiotics
*7 mm = disc size (no inhibition zone observed)

TABLE XIa

842A SPECIAL EFFECT SPECTRUM; IN VITRO STUDY

| *Escherichia coli* W-MB-60 (with special addition noted) | Test Conditions | | INHIBITION ZONE DIAMETER, mm* | | |
|---|---|---|---|---|---|
| | Inoculum ml/150 ml. | Incubation Temp. °C. | Crude 842A (Ib) 8 mg/ml | Free Acid 166 µg/ml | Sodium Salt 192 µg/ml |
| Control (no additions) | 5 | 25 | 16 | 20 | 18 |
| 0.1 M Phosphate Buffer -pH 5 | 5 | 25 | 19 | 20 | 15 |
| 0.1 M Phosphate Buffer -pH 7 | 5 | 25 | 22 | 29 | 25 |
| 0.1 M Phosphate Buffer -pH 9 | 5 | 25 | 21 | 22 | 24 |
| Human Blood Plasma 20% | 5 | 25 | 17 | 22 | 21 |
| *Cation Exchange Resin (Dow BT 91)1% | 5 | 25 | 20 | 21 | 18 |

*(Agar concentration reduced to 1% for resin plate only)

Antibiotic 842A; In Vivo: When 842A is given subcutaneously to mice it is generally more active than cephalothin and approximately equal to cephaloridine, ampicillin and chloromycetin in protecting against infection from gram-negative organisms. It is remarkably nontoxic and is rapidly excreted in the urine with approximately 79% of the subcutaneously injected 842A recovered within 4 hours.

In in vivo studies Antibiotic 842A protects against infection with three species of Proteus, two of Salmonella, one strain of *Escherichia coli*, two of Klebsiella and also against *Paracolobactrum arizonae, Aerobacter aerogenes, Pasteurella multocida* and *Diplococcus pneumoniae* 2400.

TABLE XIb

842A In Vivo Activity

| Test Organism | $ED_{50}$ by Subcutaneous Route X Two Doses |
|---|---|
| *Proteus vulgaris* | 51 µg. |
| *Proteus mirabilis* | 276 µg. |
| *Proteus morganii* 3202 | 276 µg. |
| *Salmonella schottmuelleri* | 103 µg. |
| *Klebsiella pneumoniae* AD | 125 µg. |
| *Klebsiella pneumoniae* B | 125 µg. |
| *Paracolobactrum arizonae* | 125 µg. |
| *Escherichia coli* | 200 µg. |
| *Aerobacter aerogenes* | 49 µg. |
| *Pasteurella multocida* | 57 µg. |
| *Salmonella typhosa* | 34 µg. |
| *Diplococcus pneumoniae* 2400 | 566 µg. |

THE ANTIBIOTICS

810A Fermentation: The Antibiotic 810A is produced during the aerobic fermentation of suitable aqueous nutrient mediums under controlled conditions via inoculation with the *Streptomyces griseus* culture MA-2837. Aqueous mediums such as those employed for the production of other antibiotics are also suitable for producing Antibiotic 810A. Such mediums contain sources of carbon and nitrogen assimilable by the microorganism and inorganic salts.

In general, carbohydrates such as sugars, for example, glucose, arabinose, maltose, xylose, mannitol and the like and starches such as grains, for example, oats, rye, corn starch, corn meal and the like can be used either alone or in combination as sources of assimilable carbon in the nutrient medium. The extract quantity of the carbohydrate source or sources utilized in the medium depend in part upon the other ingredients of the medium but, in general, the amount of carbohydrate usually varies between about 1 and 6% by weight of the medium. These carbon sources can be used individually or several such carbon sources may be combined in the medium. In general any proteinaceous material may be used as a nitrogen source in the fermentation process. Suitable nitrogen sources include, for example, yeast hydrolysates, yeast autolysate, soybean meal, hydrolysates of casein, corn steep liquor, distiller's solubles or tomato paste and the like. The sources of nitrogen, either alone or in combination, are used in amounts ranging from about 0.2 to 6% by weight of the aqueous medium. Typical of the mediums which are suitable for the preparation of Antibiotic 810A are those listed below. These mediums and others described in the examples which follow are merely illustrative of the wide variety of media which may be employed and are not intended to be limitative.

| Medium I: | |
|---|---|
| Difco Yeast Extract | 10.0 g. |
| Glucose | 10.0 g. |
| *Phosphate Buffer | 2.0 ml. |
| MgSO$_4$ . 7H$_2$O | 0.05 g. |
| Distilled Water | 1000.0 ml. |
| Difco Agar | 25.0 g. |
| *Phosphate Buffer: | |
| KH$_2$PO$_4$ | 91.0 g. |
| Na$_2$HPO$_4$ | 95.0 g. |
| Distilled Water | 1000.0 ml. |
| Medium II: | |
| Beef Extract | 3.0 g. |
| *NZ Amine | 10.0 g. |
| Dextrose | 10.0 g. |
| NaCl | 5.0 g. |
| Distilled H$_2$O | 1000.0 ml. |
| pH adjusted to 7.2 with NaOH | |
| *an enzymatic digested casein | |
| Medium III: | |
| Dextrose | 10.0 g. |
| Asparagine | 1.0 g. |
| K$_2$HPO$_4$ | 0.1 g. |
| MgSO$_4$ . 7H$_2$O | 0.5 g. |
| Yeast Extract | 0.5 g. |
| *Trace Element Mix No. 2 | 10.0 ml. |
| Distilled H$_2$O | 1000.0 ml. |
| pH adjusted to 7.2 with NAOH | |
| *Trace Element Mix No. 2: | |
| FeSO$_4$ . 7H$_2$O | 1.0 g. |
| MnSO$_4$ . H$_2$O | 1.0 g. |
| CuCl$_2$ . 2H$_2$O | 25.0 mg. |
| CaCl$_2$ | 100.0 mg. |
| H$_3$BO$_3$ | 56.0 mg. |
| (NH$_4$)$_6$MO$_7$O$_{24}$ . 4H$_2$O | 19.0 mg. |
| ZnSO$_4$ . 7H$_2$O | 200.0 mg. |
| Distilled H$_2$O | 1000.0 ml. |
| Medium IV: | |
| V8 Juice | 100.0 ml. |
| Staley's 4S Soybean Meal | 20.0 g. |
| Dextrose | 2.0 g. |
| Agar | 25.0 g. |
| Distilled H$_2$O | to 1000.0 ml. |
| pH 7.9-8.0 | |
| Medium V: | |
| Yeast Autolysate (Ardamine) | 10.0 g. |
| Glucose | 10.0 g. |
| *Phosphate Buffer | 2.0 ml. |
| MGSO$_4$ . 7H$_2$O | 0.05 g. |
| Distilled H$_2$O | 1000.0 ml. |
| pH - adjust to 6.5 using NaOH | |
| *Phosphate Buffer Solution: | |
| KH$_2$PO$_4$ | 91.0 g. |
| Na$_2$HPO$_4$ | 95.0 g. |
| Distilled H$_2$O | 1000.0 ml. |
| Medium VI: | |
| Corn Steep Liquor (wet basis) | 40.0 g. |
| Dextrose | 20.0 g. |
| NaCl | 2.5 g. |
| MgSO$_4$ . 7H$_2$O | 0.5 g. |
| Polyglycol 2000 | 0.25% by volume (add to each flask individually) |
| Distilled H$_2$O | 1000.0 ml. |
| pH - adjust to 7.0 with NaOH | |

| Medium VII: | Seed | Production |
|---|---|---|
| L-Asparagine | 5.0 g. | 5.0 g. |
| L-Histidine | 4.0 g. | 4.0 g. |
| DL-Phenylalanine | — | 2.0 g. |
| Monosodium glutamate | — | 1.5 g. |
| NaCl | 5.0 g. | 5.0 g. |
| K$_2$HPO$_4$ | 2.0 g. | 2.0 g. |
| CaCl$_2$ . 2H$_2$O | 0.4 g. | 0.4 g. |
| MnSO$_4$ . H$_2$O | 0.1 g. | 0.1 g. |
| FeSO$_4$ . 7H$_2$O | 0.1 g. | 0.1 g. |
| ZnSO$_4$ . 7H$_2$O | 0.05 g. | 0.05 g. |
| MgSO$_4$ . 7H$_2$O | 1.0 g. | 1.0 g. |
| Glycerol | 20.0 g. | 20.0 g. |
| Sucrose | 2.5 g. | 2.5 g. |
| Distilled H$_2$O | *1000.0 ml. | **1000.0 ml. |
| *pH adjusted to 7.0 with NaOH | | |
| **pH adjusted to 7.1 with NaOH | | |

| Medium VIII: | |
|---|---|
| Meat Extract | 0.3% |
| NaCl | 0.5% |
| NZ Amine | 1 % |
| Dextrose | 1 % |
| pH 7.0 | |

The fermentation is carried out at temperatures ranging from about 20° to 37° C.; however, for optimum results it is preferable to conduct the fermentation at temperatures of from about 22° to 30° C. The pH of the nutrient mediums suitable for growing the *Streptomyces griseus* culture (MA-2837) and producing Antibiotic 810A should be in the range of from about 5.5 to 8.0.

A small scale fermentation of Antibiotic 810A is conveniently carried out by inoculating a suitable nutrient medium with the antibiotic-producing culture and permitting the fermentation to proceed at a constant temperature of from about 24°-28° C. on a shaker over an extended period as, for example, for several days. At the end of the incubation period the mycelium is removed and the supernatant liquid is assayed.

In practice this fermentation is conducted in a sterlized flask via a one, two, three or four stage seed development. The nutrient medium for the seed stage may be any suitable combination of carbon and nitrogen sources as, for example, any one of Mediums I-VIII described above. The seed flask is shaken in a constant temperature chamber at about 28° C. for a period of from 1 to about 3 days and the resulting growth is used to inoculate either a second stage seed or the production medium. Intermediate stage seed flasks, when used, are developed in essentially the same manner, that is, the contents of the flask are used to inoculate the production medium, the inoculated flasks are shaken at a constant temperature for several days and at the end of the incubation period the contents of the flask are centrifuged to remove the mycelium. The supernatant liquid or broth is then concentrated and purified to afford the Antibiotic 810A.

For larger scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with the producing culture and the fermentation is permitted to proceed for a period of several days as, for example, from 2 to 4 days while agitating and/or aerating the nutrient medium and maintaining the temperature at about 24°–28° C. Through changes in inoculum development and changes in production medium it is possible to achieve a several-fold improvement in production and increase the potency of the antibiotic.

810A Assay Procedure Using Proteus vulgaris: Antibiotic 810A was conveniently assayed by a disc-plate procedure using *Proteus vulgaris* MB-838 (ATCC 21100 and NRRL B-3361) maintained as a slant culture on nutrient agar (Difco) plus 0.2% yeast extract (Difco) as the test organism. The inoculated slants are incubated at 37° C. for 18–24 hours and stored at refrigerator temperatures until used, fresh slants being prepared each week.

The inoculum for the assay plates is prepared each day by inoculating a 250 ml. Erlenmeyer flask containing 50 ml. of nutrient broth (Difco) plus 0.2% yeast extract (Difco) with a scraping from the slant. The flask is incubated at 37° C. on a shaking machine for 18–24 hours. The broth culture is then adjusted to 40% transmittance at a wavelength of 660 nm, using a Bausch & Lomb Spectronic 20 by the addition of a 0.2% yeast extract solution to the growth. Uninoculated broth is used as a blank for this determination. The adjusted broth (30 ml.) is used to inoculate 1 liter of medium.

Nutrient agar (Difco) plus 0.2% yeast extract (Difco) is used as the assay medium. This medium is prepared, sterlized by autoclaving and allowed to cool to 50° C. After the medium is inoculated, 10 ml. is added to each of several sterile petri dishes the medium is allowed to solidify.

Assays were run on these plates by the disc-plate procedure using 0.5 inch filter paper discs. The assay plates were incubated for 20–24 hours at 37° C. Assays are expressed as mm. diameter zone of inhibition. They were used to determine relative potencies or, when compared with a purified reference standard, the potency in $\mu g./ml.$ When such an assay is performed in a quantitative fashion from 2 to 4 $\mu g./ml.$ of antibiotic can be detected.

810A Assay Procedure Using Vibrio percolans: Assays were also run on 810A by the disc-plate procedure against *Vibrio percolans* (MB-1272) using 0.5 inch filter paper discs. The assay plates were prepared using Difco nutrient agar plus 2.0 g./liter Difco yeast extract at 10 ml. per plate. An overnight growth of the assay organism, *Vibrio percolans* (MB-1272) in nutrient broth plus 0.2% yeast extract was diluted in sterile saline solution to a suspension having 40% transmittance at a wave length of 660 m$\mu$. This suspension was added at 20 ml./liter of medium prior to pouring the plates.

The assay plates were held at 4° C. until used (5 day maximum). Following the application of antibiotic-saturated assay discs the plates were incubated at 28° C. for a period of from 8 to 24 hours. Zones of inhibition were read as mm. diameter.

Bacterial Inactivation With 810A: An in vitro study was designed to determine the resistance of Antibiotic 810A, to bacterial inactivation as compared with cephalosporin C, cephaloridine and cephalothin. This study showed that Antibiotic 810A is more stable than the latter against certain microorganisms.

The degradative bacterium used in this study was an organism known to completely inactivate cephalosporin C, namely, *Alcaligenes faecalis* (MB-9).

a. Preparation of Bacterial Cells: *Alcaligenes faecalis* (MB-9) cells were prepared as follows: the contents of an L-tube were mixed with a few ml. of nutrient broth containing 0.2% yeast extract. A loopful of the slurry was spread over the surface of a nutrient agar slant and incubated for 18 hours at 37° C. All slants were stored at 5° C. and used within 1 week after incubation. A loopful of the surface growth from each slant culture was asceptically transferred to 50 ml. of nutrient broth containing 0.2% yeast extract and shake incubated for 18 hours at 28° C. The culture was then centrifuged at 4000 rpm. for 10 minutes. The supernatant was decanted and the residual pellet of cells was washed twice with sterile 0.1 M phosphate buffer, pH 7.5 (6.8 g. of potassium phosphate and 7.1 g. of sodium hydrogen phosphate per liter of distilled water). The washed cells were then resuspended in one-tenth original volume of a 4 mg./ml. solution of antibiotic in 0.1 M phosphate buffer. The test mixture was then incubated without shaking in a water bath set at 37° C. for up to 4 hours. The test mixtures were then centrifuged at 2000 rpm. for 10 minutes and this produced a clear supernatant which was decanted into sterile tubes and immediately frozen in dry ice until ready for bioassay, usually within 3 hours. Controls were incubated in exactly the same manner, except for the absence of cells.

b. Extent of Antibiotic 810A Inactivation: The supernatants were tested for antibacterial activity in the following manner: ¼ inch diameter paper discs were moistened with the supernatants and placed on the surface of nutrient agar-yeast extract (0.2%) plates that had been previously seeded with the appropriate test organism. *B. subtilis* (MB-964) assay plates were seeded in the following manner: 5 ml. of a suspension of washed spores in 0.9% saline was added to each 150 ml. of nutrient agar-yeast extract (0.2%) of which 5 ml. was then dispensed into 15 × 100 mm. petri plates. All assay plates were stored at 5° C. and used within 3 days. Assay plates were incubated overnight at 25° C. before measurement of zones of inhibition around the test discs.

Cell-free controls of each antibiotic were assayed at 1:1, 1:2, 1:4, 1:8, 1:16 and 1:32 dilutions in order to obtain a standard reference curve. Solutions of test antibiotics were assayed at full strength after incubation in the presence of the washed bacterial cells. All samples were run in triplicate.

c. Results: Percents of inactivation were calculated by taking the average of the three zones of inhibition obtained for each test and determining the amount of antibiotic remaining in the test solution as shown by the the standard curve. This value was then subtracted from the starting concentration (4 mg./ml.) and the remainder divided by the starting concentration and multiplied by 100 to obtain the percent of inactivation. The following Tables XII and XIII demonstrate the inactivation obtained for cephalosporin C, cephalothin and Antibiotic 810A under the conditions described above.

TABLE XII

Percent Inactivation After Incubation With
Washed Bacterial Cells
(Assayed on *B. subtilis* (MB-964) Plates)
3 Hour Incubation

| Antibiotic | With *Alcaligenes faecalis* |
|---|---|
| 810A | 0 |
| Cephalosporin C | 99+ |
| Cephalothin | 62.5 |

TABLE XIII

Percent Inactivation After Incubation With
Washed Bacterial Cells
(Assayed on *V. percolans* (MB-1272) Plates)
3 Hour Incubation

| Antibiotic | With *Alcaligenes faecalis* |
|---|---|
| 810A | 0 |
| Cephalosporin C | 99+ |
| Cephalothin | 50 |

The ability of Antibiotic 810A and cephalosporin C to withstand the degradative effect of the culture *Aerobacter cloacae* (MB-2646) was also determined. This culture is gram-negative and resistant to cephalosporin C. In conducting the assay individual mixtures of the organisms and one of the antibiotic mixtures were sampled after 2 hours incubation and assayed for residual antibiotic activity. The procedure is the same assay method as described above with *Alcaligenes faecalis*. The source of the inactivating substance is a 1:160 dilution of the filtrate of an 18 hour 37° C. shake culture of *Aerobacter cloacae* MB-2646 in nutrient broth containing 0.2% yeast extract. Table XIV, infra, indicates the percent inactivation of Antibiotic 810A, cephalothin, cephaloridine and cephalosporin C on *Vibrio percolans* (MB-1272) via this method:

TABLE XIV

Percent Inactivation After Incubation With
Cell-Free Extract
(Assayed on *V. percolans* (MB-1272) Plates)
2 Hour Incubation

| Antibiotic | With *Aerobacter cloacae* |
|---|---|
| 810A | 16 |
| Cephalothin | 66 |
| Cephaloridine | 96 |
| Cephalosporin C | 96 |

Using the same assay procedure as described above, Table XV, infra, indicates the relative resistance of Antibiotic 810A to enzymatic inactivation by *Aerobacter cloacae*. The starting concentration in 250 μg./ml. Results are expressed in μg./ml.

TABLE XV

Antibiotic Activity Remaining (μg./ml.)
(Starting Concentration = 250 μg./ml.)
2 Hour Incubation

| Antibiotic | Assay Organism | With *Aerobacter cloacae** |
|---|---|---|
| 810A | *B. subtilis* 964 | 190 |
| Cephalothin | " | 140 |
| Cephaloridine | " | <10 |
| 810A | *V. percolans* 1272 | 210 |
| Cephalothin | " | 85 |
| Cephaloridine | " | <10 |

*Cell-free extract

In view of the foregoing, Antibiotic 810A is, apparently, more resistant than cephalosporin C, cephalothin and cephaloridine to inactivation by *Aerobacter cloacae*.

842A Fermentation: Antibiotic 842A is produced during the aerobic fermentation of suitable aqueous nutrient mediums under controlled conditions via inoculation with the organism *Streptomyces lactamdurans*. In general, many media which are a source of carbon and nitrogen may be used for the production of 842A. Illustrative of these are the aqueous mediums and carbohydrate and nitrogen sources described above in connection with the fermentation of 810A. The exact amount of the carbohydrate and nitrogen sources will depend upon the other ingredients comprising the fermentation medium but, in general, the amount of carbohydrate is usually about 1 to 6% by weight of the medium and the amount of available nitrogen, either alone or in combination is usually in the amount from about 0.2 to about 6% by weight of the medium. The several media described below are illustrative of those which are suitable for the preparation of Antibiotic 842A. These media are merely typical of the media which may be employed and are not intended to be limitative.

| Medium IX: | |
|---|---|
| Amber Yeast 300 | 10.0 g. |
| Distiller's Solubles | 20.0 g. |
| Dextrose | 10.0 g. |
| Distilled Water | 1000.0 ml. |
| pH 7.0 | |
| Medium X: | |
| Staley's 4S-Soybean Meal | 30.0 g. |
| Distiller's Solubles | 7.5 g. |
| Cerelose | 20.0 g. |
| NaCl | 2.5 g. |
| CaCO$_3$ (after pH to 7.0) | 10.0 g. |
| Distilled Water | 1000.0 ml. |
| Medium XI: | |
| Amber Yeast 300 | 10.0 g. |
| Distiller's Solubles | 20.0 g. |
| Distilled Water | 1000.0 ml. |
| pH 7.0 | |

The fermentation is carried out at temperatures ranging from about 20° to 37° C. but for optimum results it is preferable to conduct the fermentation at temperatures of from about 24° to 32° C. The pH of the nutrient mediums suitable for growing the *Streptomyces lactamdurans* culture (MB-2908) and producing Antibiotic 842A should be in the range of from about 6.0 to about 8.0.

A small scale fermentation of Antibiotic 842A is conveniently carried out by inoculating a suitable nutrient medium with the antibiotic-producing culture and permitting the fermentation to proceed at a constant temperature of about 28° C. on a shaker for several days. At the end of the incubation period the mycelium is removed and the supernatant liquid is assayed.

In practice, this fermentation is conducted in a sterilized flask via a one, two, three or four stage seed development. The nutrient medium for the seed stage may be any suitable combination of carbon and nitrogen sources as, for example, any one of Mediums IX-XI described above. The seed flask is shaken in a constant temperature chamber at about 28° C. for a period of from 1 to about 3 days and the resulting growth is used to inoculate either a second stage seed or the production medium. Intermediate stage seed flasks, when used, are developed in essentially the same manner, that is, the contents of the flask are used to inoculate the production medium, the inoculation flasks are shaken at a constant temperature for several days and at the end of the incubation period the contents of the flasks are centrifuged to remove the mycelium. The supernatant liquid or broth is then concentrated and purified to afford Antibiotic 842A.

For larger scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with the producing culture and the fermentation is permitted to proceed for a period of several days as, for example, from 2 to 4 days while agitating and/or aerating the nutrient medium and maintaining the temperature at about 28° C. Through changes in inoculum development and changes in production medium it is also possible to achieve a several-fold improvement in production and increase the potency of this antibiotic.

842A Assay Procedure Using *Vibrio percolans*: Assays were run by the disc-plate procedure using 0.5 inch filter paper discs. The assay plates were prepared using Difco nitrient agar plus 2.0 g./l. Difco yeast extract at 10 ml. per plate. An overnight growth of the assay organism, *Vibrio percolans* (MB-1272) in nutrient broth and 0.2% yeast extract was diluted in sterile saline solution to a suspension having 40% transmittance at a wave length of 660 nm. This suspension was added at 20 ml./liter of medium prior to pouring the plates.

The assay plates were held at 4° C. until used (5 day maximum). Following the application of the antibiotic-saturated assay discs the plates were incubated at 28° C. for a period of from 8 to 24 hours. Zones of inhibition were read as mm. diameter. They were used to determine relative potencies or, when compared with a purified reference standard, the potency in µg./ml. When such an assay is performed in a quantitative fashion from 1 to 2 µg./ml. of antibiotic can be detected.

Bacterial Inactivation With 842A: An in vitro study was designed to determine the resistance of Antibiotic 842A to bacterial inactivation as compared with cephalosporin C, cephaloridine and cephalothin. This study showed that Antibiotic 842A is more stable than the latter against certain microorganisms.

The degradative bacteria used in the study were two organisms known to completely inactivate cephalosporin C, namely, *Alcaligenes faecalis* (MB-9) and *Alcaligenes viscosus* (MB-12).

a. Preparation of Bacterial Cells: *Alcaligenes viscosus* (MB-12) and *A. faecalis* (MB-9) cells were prepared as follows: the contents of an L-tube were mixed with a few ml. of nutrient broth containing 0.2% yeast extract. A loopful of the slurry was spread over the surface of a nutrient agar slant and incubated for 18 hours at 37° C. All slants were stored at 5° C. and used within 1 week after incubation. A loopful of the surface growth from each slant culture was asceptically transferred to 50 ml. of nutrient broth containing 0.2% yeast extract and shake incubated for 18 hours at 28° C. The culture was then centrifuged at 4000 rpm. for 10 minutes. The supernatant was decanted and the residual pellet of cells was washed twice with sterile 0.1 M phosphate buffer, pH 7.5 (6.8 g. of potassium phosphate, i.e., $KH_2PO_4$ and 7.1 g. of sodium hydrogen phosphate per liter of distilled water). The washed cells were then resuspended in one-tenth original volume of a 4 mg./ml. solution of antibiotic in 0.1 M phosphate buffer. The test mixture was then incubated without shaking in a water bath set at 37° C. for 4 hours. The test mixtures were then centrifuged at 2000 rpm. for 10 minutes and this produced a clear supernatant which was decanted into sterile tubes and immediately frozen in dry ice until ready for bioassay, usually within three hours. Controls were incubated in exactly the same manner, except for the absence of cells.

b. Extent of Antibiotic 842A Inactivation: The supernatants were tested for antibacterial activity in the following manner: ¼ inch diameter paper discs were moistened with the supernatant and placed on the surface of nutrient agar-yeast extract (0.2%) plates that had been previously seeded with the appropriate test organism. *B. subtilis* (MB-964) assay plates were seeded in the following manner: 5 ml. of a suspension of washed spores in 0.9% saline was added to each 150 ml. of a 2% nutrient agar-yeast extract (45° C.) of which 5 ml. was then dispensed into 15 × 100 mm. petri plates. All assay plates were stored at 5° C. and used within 3 days. Assay plates were incubated overnight at 25° C. before measurement of zones of inhibition around the test discs.

Cell-free controls of each antibiotic were assayed at 1:1, 1:2, 1:4, 1:8, 1:16 and 1:32 dilutions in order to obtain a standard reference curve. Solutions of test antibiotics were assayed at full strength after incubation in the presence of the washed bacterial cells. All samples were run in triplicate.

c. Results: Percents of inactivation were calculated by taking the average of the three zones of inhibition obtained for each test and determining the amount of antibiotic remaining in the test solution as shown by the standard curve. This value was then subtracted from the starting concentration (4 mg./ml.) and the remainder divided by the starting concentration and multiplied by 100 to obtain the percent of inactivation. The following Table XVI demonstrates the inactivation obtained for cephalosporin C and Antibiotic 842A under the conditions described above.

TABLE XVI

| DEGRADATIVE ORGANISM | Percent Inactivation After Incubation With Washed Bacterial Cells (Assayed on *B. subtilis* (MB-964) Plates) 4 Hour Incubation | |
|---|---|---|
| | Ceph C | Antibiotic 842A |
| *Alcaligenes faecalis* MB-9 | 99+ | 0 |
| *A. viscosus* MB-12 | 99+ | 54.4 |

The ability of Antibiotic 842A and cephalosporin C to withstand the degradative effect of four other cultures was also determined. These cultures are: *Escherichia coli* 236, *Proteus morganii* 251, *Proteus morganii* 356 and *Proteus mirabilis* 241. Each is gram-negative and resistant to cephalosporin C. In conducting the assay, individual mixtures of the organisms and one of the antibiotics were sampled after 4 hours incubation and assayed for residual antibiotic activity. The procedure is the same assay method as described above against *Alcaligenes faecalis* MB-9 and *A. viscosus* MB-12. The following table indicates the percent inactivation of cephalosporin C and 842A on *B. subtilis* (MB-964) via this method:

TABLE XVII

| Culture | Ceph C | Antibiotic 842A |
|---|---|---|
| *Escherichia coli* 236 | >99 | 38 |
| *Proteus morganii* 251 | >99 | 80 |
| *Proteus morganii* 356 | >99 | 69 |
| *Proteus mirabilis* 241 | 72 | 5 |

The foregoing data indicates that Antibiotic 842A is, apparently, more resistant than cephalosporin C to inactivation by *A. faecalis, A. viscosus, Escherichia coli* 236, *Proteus morganii* 251, *Proteus morganii* 236 and *Proteus mirabilis* 241.

The Antibiotic 842A which is obtained via the instant fermentation process is an amphoteric compound with an apparent isoelectric point of about pH 3.5; it is unstable above pH 9.0 but relatively stable at pH 1.5.

Since Antibiotic 810A and Antibiotic 842A and their salts effectively inhibit the growth of various species of Salmonella they can be used as disinfectants in various household and industrial applications. For example, 810A exhibits activity against *Salmonella schottmuelleri* and *S. gallinarum* and 842A exhibits activity against *Salmonella schottmuelleri* 3010, *S. gallinarum* and *S. typhosa* and this property is indicative of their usefulness as sanitizing agents in household and industrial applications.

ISOLATION AND PURIFICATION

Antibiotic 810A: Antibiotic 810A can be purified by adsorption on an ion exchange resin as, for example, on synthetic anion exchange resins derived from dextrose or acrylic copolymers or non-ionic cross-linked polymers. The adsorbed antibiotic is eluted fom the resin or polymer adsorbate with water or with an aqueous alcoholic solution of a suitable salt such as ammonium chloride or sodium chloride and the like. Illustrative of the ion exchange resins and polymers which may be employed are, for example, the DEAE Sephadex A-25, Amberlite IRA-68 and Amberlite XAD-2 mediums described below. If desired the eluate obtained according to the foregoing procedure can be further purified by a second and third adsorption and elution step. Concentratesof all the eluates are then obtained to afford the purified product.

810A Components: Antibiotic 810A can be separated into its components, 7β-(D-5-amino-5-carboxyvaleramido)-3-(α-methoxy-p-sulfooxycinnamoyloxymethyl)-7-methoxy-3-cephem-4-carboxylic acid and 7β-(D-5-amino-5-carboxyvaleramido)-3-(α-methoxy-p-hydroxycinnamoyloxymethyl)-7-methoxy-3-cephem-4-carboxylic acid, by chromatographic means. These include:

1. Chromatography on a strongly hydrophylic anion exchange resin such as *DEAE Sephadex A-25, developed with an ammonium bromide-formic acid system. Various concentration of this system may be employed but, in practice, a 0.5 M ammonium bromide-0.1 M formic acid solution is preferred.
2. Chromatography on a weakly basic anion exchange resin such as **Amberlite IRA-68. This is a group separation where material in crude form is fed at a pH of about 3 to 3.5 and eluted first with an acid at a pH of about 2 and then with NaCl/HCl at a pH of about 1.
3. Chromatography on a non-ionic cross-linked polystryene polymer such as ***Amberlite XAD-2. Elution is effected with a suitable aqueous system but, in general, it is most advantageous to employ a mixture of water and a lower alkyl ketone. Typical of the eluants which may be employed are, for example, 10% methanol in water followed by 50% methanol in water. Alternatively, 20% acetone in water can be substituted for the 50% methanol in water solution.

DEAE Sephadex A-25 is a synthetic anion exchange resin derived from the polysaccharide, dextran in its chloride form, i.e., with chloride counter ions; Pharmacia Fine Chemicals, Inc., .800 Centenial Avenue, Piscataway, New Market, New Jersey 08854.

A synthetic anion exchange resin; a cross-linked acrylic copolymer containing weakly basic tertiary amino groups; Rohm & Haas Co., Philadelphia, Pennsylvania 19105. A non-ionic cross-linked polystyrene polymer sorbent; Rohm & Haas Co., Philadelphia, Pennsylvania 19105.

The individual products obtained via the above methods may be purified by rechromatography. Thus, for example, 7β-(D-5-amino-5-carboxyvaleramido)-3-(α-methoxy-p-sulfooxycinnamoyloxymethyl)-7-methoxy-3-cephem-4-carboxylic acid (Ic) may be repurified by subjecting that product to the purification method described in Method 1, supra, followed by desalting on Amberlite XAD-2 absorbent; and 7β-(D-5-amino-5-carboxyvaleramido)-3-(α-methoxy-p-hydroxycinnamoyloxymethyl)-7-methoxy-3-cephem-4-carboxylic acid may be repurified by rechromatography on a Sephadex A-25 anion exchange resin developed with 0.5 M ammonium bromide and 0.05 M acetic acid.

Antibiotic 842A: The Antibiotic 842A can be purified by adsorption on an ion exchange resin as, for example, on resins composed of quaternary ammonium or sulfonic acid exchange media. The adsorbed antibiotic is eluted from the resin adsorbate with aqueous solutions or with an aqueous alcoholic solution of a suitable salt such as ammonium chloride, sodium chloride and the like. Suitable ion exchange resins which may be employed include, for example, the polystyrene nuclear sulfonic acid resins (45 or 53% water) or polystyrene trimethylbenzylammonium resins (43% water) which are known as Dowex 50 and Dowex 1, respectively. If desired the eluate obtained according to the foregoing procedure can be further purified by a second and third adsorption and elution step. Concentrates of all the eluates are then obtained to afford the purified 842A product.

FORMULATIONS

Antibiotic 810A and its individual components and Antibiotic 842A may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include; for example, mannitol, sucrose, glucose or sterile liquids such as water, saline, glycols and oils of a petroleum, animal, vegetable or synthetic origin as, for example peanut oil, mineral oil or sesame oil. Also, in addition to a carrier the instant compositions may also include other ingredients such as stabilizers, binders, antioxidants, preservatives, lubricators, suspending agents, viscosity agents, flavoring agents, and the like. In addition, there may also be included in the composition other active ingredients to provide a broader spectrum of antibiotic activity.

The dosage to be administered depends to a large extent upon the condition of the subject being treated and the weight of the host. The parenteral route being preferred for generalized infections and the oral route for intestinal infections. In general, a daily dosage consists of from about 15 to about 175 mg. of active ingredient per kg. of body weight of the subject in one or more applications per day. A preferred daily dosage for Antibiotic 810A or its individual components lies in the range of from about 20 to 40 mg. of active ingredient per kg. of body weight. The preferred daily dosage for Antibiotic 842A is in the range of from about 40 to 80 mg. of active ingredient per kg. of body weight.

The instant compositions may be administered in several unit dosage forms as, for example, in solid or liquid orally ingestible dosage forms. The compositions, per unit dosage, whether liquid or solid, will generally contain from about 15 to about 700 mg. by weight of the active ingredient based upon the total of the compositions; however, in general, it is preferable to employ a dosage amount in the range of from about 80 to 320 mg. In parenteral administration the unit dosage is usually the pure compound in a sterile water solution or in the form of a soluble powder intended for solution.

One typical unit dosage form consists in mixing 120 mg. of Antibiotic 810A or 120 mg. of one of its components or salt thereof, with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules may be employed. In a similar manner other unit dosages such as compressed tablets and pills can also be prepared. The following examples are illustrative:

| Dry-filled Capsule Containing 120 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| | Per Capsule |
| 7β-(D-5-amino-5-carboxyvaleramido)-3-(α-methoxy-p-sulfooxycinnamoyloxymethyl)-7-methoxy-3-cephem-4-carboxylic Acid (Ic) | 120 mg. |
| Lactose | 20 mg. |
| Magnesium Stearate | 5 mg. |
| Capsule Size No. 3 | 145 mg. |

The 7β-(D-5-amino-5-carboxyvaleramido)-3-(α-methoxy-p-sulfooxycinnamoyloxymethyl)-7-methoxy-3-cephem-4-carboxylic acid (Ic) is reduced to a No. 60 powder and then lactose and magnesium stearate are passed through a No. 60 bolting cloth onto the powder and the combined ingredients admixed for 10 minutes and then filled into No. 3 dry gelatin capsules.

By substituting 40 mg. of Antibiotic 842A and 100 mg. of lactose for the 120 mg. of active ingredient and 20 mg. of lactose recited in the foregoing formulation, there is thus obtained a 145 mg. capsule which is also suitable for oral administration.

| Tablet Containing 250 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| | Per Tablet |
| 7β-(D-5-amino-5-carboxyvaleramido)-3-(α-methoxy-p-sulfooxycinnamoyl-oxymethyl)-7-methoxy-3-cephem-4-carboxylic Acid (Ic) | 250. mg. |
| Dicalcium Phosphate, U.S.P. | 192. mg. |
| Magnesium Stearate | 5. mg. |
| Lactose, U.S.P. | 65. mg. |

The active component is blended with the dicalcium phosphate and lactose. The mixture is granulated with 15% cornstarch paste (6 mg.) and rough-screened. It is dried at 45° C. and screened again through a No. 16 screen. The magnesium stearate is added and the mixture is compressed into tablets approximately 0.5 inch in diameter.

| Tablet Containing 7β-(D-5-amino-5-carboxyvaleramido)-3-(carbamoyloxymethyl)-7-methoxy-3-cephem-4-carboxylic Acid (Ib) | |
|---|---|
| | Per Tablet |
| 7β-(D-5-amino-5-carboxyvaleramido)-3-(carbamoyloxymethyl)-7-methoxy-3-cephem-4-carboxylic Acid (Ib) | 125. mg. |
| Cornstarch, U.S.P. | 6. mg. |
| Dicalcium Phosphate | 192. mg. |
| Lactose, U.S.P. | 190. mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| Parenteral Solution Containing 500 mg. of 7β-(D-5-amino-5-carboxyvaleramido)-3-(α-methoxy-p-sulfooxycinnamoyloxymethyl)-7-methoxy-3-cephem-4-carboxylic Acid (Ic) | |
|---|---|
| Ampoule: | |
| 7β-(D-5-amino-5-carboxyvaleramido)-3-(α-methoxy-p-sulfooxycinnamoyloxymethyl)-7-methoxy-3-cephem-4-carboxylic Acid (Ic) | 500 mg. |
| Ampoule: | |
| Diluent: Sterile Water for Injection | 2 cc. |

The 7β-(D-5-amino-5-carboxyvaleramido)-3-(α-methoxy-p-sulfooxycinnamoyloxymethyl)-7-methoxy-3-cephem-4-carboxylic acid (Ic) may be administered alone or in combination with other biologically active ingredients as, for example, with other antibacterial agents such as lincomycin, a penicillin, streptomycin, novobiocin, gentamicin, neomycin, colistin and kanamycin.

By substituting an equivalent amount of 7β-(D-5-amino-5-carboxyvaleramido)-3-(carbamoyloxymethyl)-7-methoxy-3-cephem-4-carboxylic acid (Ib) for the 500 mg. of 7β-(D-5-amino-5-carboxyvaleramido)-3-(α-methoxy-p-sulfooxycinnamoyloxymethyl)-7-methoxy-3-cephem-4-carboxylic acid (Ic) recited in the foregoing formulation, there is also obtained a formulation suitable for parenteral administration.

The products of this invention (I) form a wide variety of pharmacologically acceptable salts with inorganic and organic bases; these include, for example, metal salts such as are derived from alkali metal and alkaline earth metal hydroxides, carbonates and bicarbonates and salts derived from primary, secondary, and tertiary amines such as monoalkylamines, dialklamines, trialkla- mines, lower alkanolamines, di-lower alkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples of these salts include salts derived from sodium hydroxide, sodium carbonate, sodium bicarbonate, potassium carbonate, potassium hydroxide, calcium carbonate and the like and salts derived from such amines as trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline and N-methylglucamine and the like.

The aforementioned salts can be mono-salts such as the monosodium salt obtained, for example, by treating one equivalent of sodium or calcium hydroxide with one equivalent of product (I), mixed di-salts obtained by treating one equivalent of the mono-salt with one equivalent of a different base. Alternatively, the said di-salts can be obtained by treatment with two equivalents of a base such as sodium hydroxide or calcium hydroxide with one equivalent of the said product (I). In addition, mixed salts and esters such as those obtained by treating the product (I) with one equivalent of sodium hydroxide and then with one equivalent of lactic acid are also contemplated.

The salts of this invention are pharmacologically acceptable nontoxic derivatives which can be used as the active ingredient in suitable unit-dosage pharmaceutical forms. Also, they may be combined with other drugs to provide compositions having a broad spectrum of activity. In addition, the instant salts and, also, the corresponding ester and amide derivatives, have utility as intermediates in preparing the carboxylic acid product illustrated by formula I, supra. And too, the said salts may be used to prepare other pharmaceutically acceptable salts.

In addition to salts the instant products (I) may also be converted to their corresponding mono- and di-esters and mono- and diamides as, for example, the pivaloyloxymethyl, or dibenzhydryl esters or alkyl, cycloalkyl, aryl or aralkyl esters as, for example, the methyl, ethyl, cyclohexyl, phenyl and benzyl esters or amides, diamides, N-lower alkyl amides, N,N-di-lower alkylamides, N-aralkylamides, N,N-diaralkylamides or heterocyclic amides such as the N-methyl and N-ethylamide, N,N-dimethylamide, N,N-diethylamide, N-benzylamide, N,N-dibenzylamide, piperidide, pyrrolidide or morpholide and the like.

Methods for the preparation of the aforementioned esters and amide derivatives include the reaction of the carboxylic acid product (I) or corresponding acid halide with methanol, ethanol, cyclohexanol, phenol, benzyl-alcohol or dibenzhydrol. In a similar manner the amide derivatives may be obtained by treating the corresponding acid halide with ammonia or with the appropriate alkylamine, dialkylamine, aralkylamine or heterocyclic amine. These and other conventional methods for the preparation of the said esters and amides will be obvious to those skilled in the art.

The examples which follow illustrate the methods by which the products of this invention may be obtained. However, the examples are illustrative only and it should be apparent to those having ordinary skill in the art that this invention includes other functionally equivalent products and methods for their preparation. Therefore, any modification of this synthesis which results in the formation of an identical product should be construed as constituting an analogous method. The claimed process is capable of wide variation and modification and, therefore, any minor departure therefrom or extension thereof is considered as being within the skill or the artisan and as falling within the scope of this invention.

EXAMPLE 1

Antibiotic 810A

A lyophilized tube of *streptomyces griseus* culture (MA-2837) was opened aseptically. The contents were used to inoculate four slants of a nutrient medium having the following composition:

| Medium I: | | |
|---|---|---|
| Difco Yeast Extract | 10.0 | g. |
| Glucose | 10.0 | g. |
| *Phosphate Buffer | 2.0 | ml. |
| $MgSO_4 . 7H_2O$ | 0.05 | g. |
| Distilled Water | 1000.0 | ml. |
| Difco Agar | 25.0 | g. |
| *Phosphate Buffer: | | |
| $KH_2PO_4$ | 91.0 | g. |
| $Na_2HPO_4$ | 95.0 | g. |
| Distilled Water | 1000.0 | ml. |

The slants were prepared by dispensing 14 ml./22 × 75 mm. culture tube. The tube was then stoppered with cotton, heated at 120° C. for 15 minutes to effect sterilization and the medium allowed to solidify in a slanted position. The inoculated slants were incubated at 28° C. for 1 week and then stored at 4° C. until used. The culture on one of these slants was then used to inoculate baffled Erlenmeyer flasks (250 ml.) containing 50 ml. of Medium II, infra, by the addition of 5 ml. of sterile medium, scraping the slant surface to suspend the growth and aseptically pipetting 1 ml. into each of three seed flasks. Medium II has the following composition:

| Medium II: | | |
|---|---|---|
| Beef Extract | 3.0 | g. |
| *NZ Amine | 10.0 | g. |
| Dextrose | 10.0 | g. |
| NaCl | 5.0 | g. |
| Distilled Water | 1000.0 | ml. |
| pH adjusted to 7.2 with NaOH | | |
| *An enzymatic digested casein | | |

The seed flask was shaken on a 220 rpm. rotary shaker with a 2 inch throw for 3 days. The seed flask culture was then used to inoculate 11 2-liter baffled Erlenmeyer flasks each containing 350 ml. of Medium III using a 2–3% inoculum. Medium III has the following composition:

| Medium III: | | |
|---|---|---|
| Dextrose | 10.0 | g. |
| Asparagine | 1.0 | g. |
| $K_2HPO_4$ | 0.1 | g. |
| $MgSO_4 . 7H_2O$ | 0.5 | g. |
| Yeast Extract | 0.5 | g. |
| *Trace Element Mix No. 2 | 10.0 | ml. |
| Distilled Water | 1000.0 | ml. |
| pH adjusted to 7.2 with NaOH | | |
| *Trace Element Mix No. 2: | | |
| $FeSO_4 . 7H_2O$ | 1.0 | g. |
| $MnSO_4 . H_2O$ | 1.0 | g. |
| $CuCl_2 . 2H_2O$ | 25.0 | mg. |
| $CaCl_2$ | 100.0 | mg. |
| $H_3BO_3$ | 56.0 | mg. |
| $(NH_4)_6MO_7O_{24} . 4H_2O$ | 19.0 | mg. |
| $ZnSO_4 . 7H_2O$ | 200.0 | mg. |
| Distilled Water | 1000.0 | ml. |

The flasks were then shaken on a 135–150 rpm. shaker with a 2 inch throw for 4 days at 28° C. At the end of the incubation period the contents of the 11 flasks were combined and assayed. The assay on the combined, centrifuged broth showed an inhibition zone of 22 mm. (½ inch discs) against *Proteus vulgaris* on a standard assay plate. This antibiotic was identified as 810A, that is, an antibiotic mixture comprising 7β-(D-5-amino-5-carboxyvaleramido)-3-(α-methoxy-p-sulfooxycinnamoyloxymethyl)-7-methoxy-3-cephem-4-carboxylic acid and 7β-(D-5-amino-5-carboxyvaleramido)-3-(α-methoxy-p-hydroxycinnamoyloxymethyl)-7-methoxy-3-cephem-4-carboxylic acid (Ia).

EXAMPLE 2

Antibiotic 810A

A lyophilized tube of *Streptomyces griseus* (MA-2837) was opened asceptically and the contents were used to inoculate the nutrient medium slants described as Medium I in Example 1. These slants were incubated at 28° C. for 1 week after which they were stored at 4° C. A portion of the culture on one of these slants was then used to inoculate a 250 ml. baffled Erlenmeyer seed flask containing 50 ml. of the medium described as Medium II in Example 1. This inoculated medium was incubated at 28° C. for 2 days on a 220 rpm. rotary shaker with a 2 inch throw. The inoculum was then washed asceptically by centrifuging down the mycelia, pouring off the supernatant, resuspending in an equal volume of saline solution, re-centrifuging and again resuspending in a 0.9% sodium chloride solution. The washed mycelia was then used to inoculate (2% inoculum) two 250 ml. baffled Erlenmeyer flasks each containing 50 ml. of a chemically defined production medium which has been sterilized at 120° C. for 15 minutes. The chemically defined production medium has the following composition.

| Production Medium: | | |
|---|---|---|
| L-Proline | 15.0 | g. |
| Glycerol | 20.0 | g. |
| Sucrose | 2.5 | g. |
| Monosodium glutamate | 1.5 | g. |
| NaCl | 5.0 | g. |
| $K_2HPO_4$ | 2.0 | g. |
| $CaCl_2$ | 0.4 | g. |
| $MnCl_2 . 4H_2O$ | 0.1 | g. |
| $FeCl_3 . 6H_2O$ | 0.1 | g. |
| $ZnCl_2$ | 0.05 | g. |
| $MgSO_4 . 7H_2O$ | 1.0 | g. |
| Distilled Water | 1000.0 | ml. |
| pH (unadjusted) 7.1 | | |

The production flasks were then shaken at 220 rpm. on a shaker with a 2 inch throw for 4 days at 28° C. Assays were run at 3 and 4 days. Samples were centrifuged and the supernatants assayed by the disc-Petri plate procedure. Using ¼ inch discs these broths gave inhibition zones against *Proteus vulgaris* (MB-838) of 21 mm. after 3 days and 26 mm. after 4 days. The product was identified as Antibiotic 810A.

EXAMPLE 3

Antibiotic 810A

A lyophilized tube of *Streptomyces griseus* (MA-4125a; a natural subisolate of MA-2837) was opened asceptically and the contents transferred onto slants of the following composition:

| Medium IV: | | |
|---|---|---|
| V8 Juice | 100 | ml. |
| Staley's 4S-Soybean Meal | 20.0 | g. |
| Dextrose | 2.0 | g. |
| Agar | 25.0 | g. |
| Distilled Water | to 1000.0 | ml. |
| pH 7.9 - 8.0 | | |

The slants thus obtained were then used to inoculate several Erlenmeyer flasks (250 ml.) each containing 50 ml. of Medium V, infra.

| Medium V: | | |
|---|---|---|
| Yeast Autolysate (Ardamine) | 10.0 | g. |
| Glucose | 10.0 | g. |
| *Phosphate Buffer | 2.0 | ml. |
| $MgSO_4 . 7H_2O$ | 0.05 | g. |
| Distilled Water | 1000.0 | ml. |
| pH - adjust to 6.5 using NaOH | | |
| *Phosphate Buffer Solution: | | |
| $KH_2PO_4$ | 91.0 | g. |
| $Na_2HPO_4$ | 95.0 | g. |
| Distilled Water | 1000.0 | ml. |

The seed flasks were shaken for 1 day at 220 rpm. at 28° C.

The contents of the flasks were then used to inoculate 39 unbaffled Erlenmeyer flasks (250 ml.) containing 40 ml. of the Medium VI, infra, at 3.5 ml. of inoculum per flask.

| Medium VI: | | |
|---|---|---|
| Corn Steep Liquor (wet basis) | 40.0 | g. |
| Dextrose | 20.0 | g. |
| NaCl | 2.5 | g. |
| $MgSO_4 . 7H_2O$ | 0.5 | g./liter |
| Polyglycol 2000 | 0.25% | by volume (add to each flask individually) |
| Distilled Water | 1000.0 | ml. |
| pH - adjust to 7.0 with NaOH | | |

The production flasks were shaken on a rotary shaker with a 2-inch throw at 220 rpm. and at 24° C. for 40 hours after which time the flasks were pooled, an aliquot was taken for assay and the remainder delivered for extraction studies. The sample for assay was acidified to pH 4.0 using hydrochloric acid, filtered, diluted 1:4 in pH 5.0 phosphate buffer and placed onto *Proteus vulgaris* MB-838 plates using ¼ inch discs. The zone of inhibition was 26.5 mm. The product was identified as Antibiotic 810A but primarily it consisted of 7β-(D-5-amino-5-carboxyvaleramido)-3-(α-methoxy-p-sulfooxycinnamoyloxymethyl-7-methoxy-3-cephem-4-carboxylic acid with only trace amounts of 7β-(d-5-amino-5-carboxyvaleramido)-3-(α-methoxy-p-hydroxycinnamoyloxymethyl)-7-methoxy-3-cephem-4-carboxylic acid.

EXAMPLE 4

Antibiotic 810A

A V8 medium slant of the *Streptomyces griseus* culture (MA-4125a) was used to inoculate 50 ml. of Medium V in a 250 ml. baffled Erlenmeyer flask.

| Medium V: | | |
|---|---|---|
| Yeast Autolysate (Ardamine) | 10.0 | g. |
| Glucose | 10.0 | g. |
| *Phosphate Buffer | 2.0 | ml. |
| $MgSO_4 . 7H_2O$ | 0.05 | g. |
| Distilled $H_2O$ | 1000.0 | ml. |
| pH adjusted to 6.5 with NaOH | | |
| *Phosphate Buffer: | | |
| $KH_2PO_4$ | 91.0 | g. |
| $Na_2HPO_4$ | 95.0 | g. |
| Distilled $H_2O$ | 1000.0 | ml. |

The flask was then shaken on a rotary shaker at 220 rpm. for 1 day at 28° C. Three ml. of this vegetative inoculum was used to inoculate a seed flask containing 50 ml. of the following synthetic medium (Medium VII) in a 250 ml. baffled Erlenmeyer flask.

| Medium VII: | Seed | Production |
|---|---|---|
| L-Asparagine | 5.0 g. | 5.0 g. |
| L-Histidine | 4.0 g. | 4.0 g. |
| DL-Phenylalanine | — | 2.0 g. |
| Monosodium glutamate | — | 1.5 g. |
| NaCl | 5.0 g. | 5.0 g. |
| K$_2$HPO$_4$ | 2.0 g. | 2.0 g. |
| CaCl$_2$ . 2H$_2$O | 0.4 g. | 0.4 g. |
| MnSO$_4$ . H$_2$O | 0.1 g. | 0.1 g. |
| FeSO$_4$ . 7H$_2$O | 0.1 g. | 0.1 g. |
| ZnSO$_4$ . 7H$_2$O | 0.05 g. | 0.05 g. |
| MgSO$_4$ . 7H$_2$O | 1.0 g. | 1.0 g. |
| Glycerol | 20.0 g. | 20.0 g. |
| Sucrose | 2.5 g. | 2.5 g. |
| Distilled H$_2$O | *1000.0 ml. | **1000.0 ml. |

*pH adjusted to 7.0 with NaOH
**pH adjusted to 7.1 with NaOH

The seed flask was again shaken at 220 rpm. for 1 day at 28° C. This synthetic seed was then used to inoculate several 250 ml. unbaffled Erlenmeyer flasks containing 38 ml. of Medium VII production, supra, at 1.5 ml. of inoculum per flask. The production flasks were shaken at 220 rpm. and 24° C. and their contents were then pooled and assayed at 4 and 5 days ago. In the assay the whole broth was acidified to pH 4.0 using hydrochloric acid and the broth was then filtered and diluted 1:4 in pH 5.0 phosphate buffer. The assay was run on *Proteus vulgaris* MB-38 using 0.5 inch discs. An inhibition zone of 25.5 mm. was obtained with this fermentation broth after 4 days incubation and the product thus obtained was identified as 810A.

EXAMPLE 5

Preparation of Antibiotic 810A and Separation into Components

Step A: Fermentation

Stage 1: The contents of a lyophilized tube of *Streptomyces griseus* (MA-2837) was suspended in 2 ml. of Medium I (described in Example 1) and the resulting inoculum was used to inoculate slants of the same medium. These slants were incubated at 28° C. for 5 days or until well-sporulated and then 10 ml. of Medium VIII, infra, was added to the slants.

| Medium VIII: | |
|---|---|
| Meat Extract | 0.3% |
| NaCl | 0.5% |
| NZ Amine | 1% |
| Dextrose | 1% |
| pH 7.0 | |

The growth on each slant was scraped into suspension and the suspension was used as the inoculum in Stage 2, infra.

Stage 2: The suspension obtained in Stage 1 was used to inoculate a 250 ml. baffled Erlenmeyer flask containing 50 ml. of sterilized Medium VIII (described in Stage 1). The inoculated flask was then placed on a 220 rpm. rotary shaker and incubated for 48 hours at 28° C.

Stage 3: The contents of an inoculum flask from Stage 2 was used to inoculate a 2-liter baffled Erlenmeyer flask containing 500 ml. of the medium identified as Medium VIII in Stage 1. The inoculated flask was then placed on a 220 rpm. rotary shaker and incubated for 48 hours at 28° C.

Stage 4: An inoculum of 500 ml. of the resulting growth from Stage 3 was used to inoculate a 200 gallon stainless steel fermentor containing 467 liters of a sterile Medium VIII (described in Stage 1). The fermentation was allowed to proceed at a temperature of 28° C. with agitation (130 rpm.) while maintaining an air flow of 10 cfm for 65 hours. During the fermentation an antifoam agent, Polyglycol 2000, was added in small quantities to prevent excessive foaming.

Stage 5: An inoculum of 100 gallons of the resulting growth from Stage 4 was used to inoculate a 1500 gallon stainless steel fermentor containing 1200 gallons of Medium IX, infra.

| Medium IX: | |
|---|---|
| Corn Steep Liquor | 4% |
| Dextrose | 2% |
| pH adjusted to 7.2 with NaOH | |

The fermentation was allowed to proceed at a temperature of 28° C. with agitation (120 rpm). While maintaining an air flow of 55.3 cfm for 30–36 hours. During the fermentation Polyglycol 2000 was added in small quantities to prevent excess foaming. The batch was harvested and activity was determined by disc-plate assay. Using 0.5 inch discs this broth gave an inhibition zone of 32.5 mm. against *Proteus vulgaris* MB-838 when harvested at 31 hours age.

Step B: Isolation of Antibiotic Mixture 810A

Filtered broth (1075 gal.) from Step A, Stage 5, was harvested after 36 hours and the pH adjusted from the range of 7–8 to 3.0 in the fermentor by the addition of phosphoric acid. The mycelia were removed by passage through a plate-screen type filter press and discarded. The filtered broth was then passed through a 100 gal. bed of Amberlite XAD-2 adsorbent resin at a flow rate of 10 gallons per minute. The spent broth was assayed and discarded and the resin bed was washed with two volumes of water. The antibiotic was eluted from the resin bed with a 60% solution of methanol and water at a flow rate of 5 gallons per minute. Forty fractions, each 5 gallons, were collected and assayed. Fractions 2 through 40 were combined and the methanol was removed by vacuum evaporation. The final concentrate (41.5 gal.) was adjusted to pH 3.5 by the addition of ammonium hydroxide and held frozen.

Samples were bio-assayed be the disc-plate method against *Proteus vulgaris*.

Filtered Broth: Assays run on 1060 gallons of filtered broth gave the following zone diameters.

| Filtered Broth | |
|---|---|
| Dilution | Zone Size |
| 1:2 | 26.8 mm. |
| 1:4 | 23.8 mm. |
| 1:8 | 21.1 mm. |

Spent Broth and Wash: Ten fractions of 100 gallons each assayed zero without dilution. The water wash assayed zero.

Eluate Fractions: Assays were run on all fractions. The zone diameters are tabulated below:

| Eluate Fractions | | | |
|---|---|---|---|
| Fraction | Zone Size | Fraction | Zone Size |
| 1 | 0 | 21 | 33 mm. |
| 2 | 28 mm. | 22 | 33 |
| 3 | 35 | 23 | 34 |
| 4 | 34 | 24 | 34 |
| 5 | 36 | 25 | 33 |
| 6 | 36 | 26 | 34 |
| 7 | 36 | 27 | 32 |

-continued

| Eluate Fractions | | | |
|---|---|---|---|
| Fraction | Zone Size | Fraction | Zone Size |
| 8 | 38 | 28 | 33 |
| 9 | 38 | 29 | 32 |
| 10 | 36 | 30 | 32 |
| 11 | 36 | 31 | 32 |
| 12 | 38 | 32 | 30 |
| 13 | 40 | 33 | 30 |
| 14 | 37 | 34 | 30 |
| 15 | 36 | 35 | 28 |
| 16 | 37 | 36 | 27 |
| 17 | 38 | 37 | 28 |
| 18 | 36 | 38 | 26 |
| 19 | 36 | 39 | 26 |
| 20 | 35 | 40 | 26 |

Eluate Composite and Eluate Concentrate: Assays were also run on 195 gallons of eluate composite and 41.5 gallons of Antibiotic 810A in the form of eluate concentrate.

| Eluate Composite | | Eluate Concentrate 810A | |
|---|---|---|---|
| Dilution | Zone Size | Dilution | Zone Size |
| 1:5 | 28.8 mm. | 1:16 | 27.25 mm. |
| 1:10 | 27.0 mm. | 1:32 | 24.5 mm. |
| 1:20 | 23.8 mm. | | |
| 1:40 | 21.0 mm. | | |

| Total Solids Assay: | | |
|---|---|---|
| Filtered Broth | 119 | kg. |
| 195 Gallon Eluate Composite | 7.23 | kg. |
| 41.5 Gallon Eluate Concentrate | 7.20 | kg. |

Step C: Adsorption on an Anion Exchange Resin

The concentrate from Step B (20.7 gal.) was diluted to 31 gallons with water and adsorbed on a 22.5 liter bed of weakly basic anion exchange resin (Amberlite IRA-68 resin on the chloride cycle) at pH 4.0 and a flow of 2 gallons per minute. This was followed by a 45 liter water wash whereafter the resin bed was eluted with a pH 7.5 solution of 1 M sodium nitrate and 0.1 M sodium acetate at a flow rate of 1.5 liters per minute. Ten 5-gallon eluate fractions were then collected and the pH adjusted to 4 with hydrochloric acid as collected.

All fractions were bio-assayed by the disc-plate method against *Proteus vulgaris* as follows:

| Feed Solution | | | Eluate Fractions; Dilution 1:10 | | | | |
|---|---|---|---|---|---|---|---|
| Dilution | Zone Size | | Fraction | Zone Size | | Fraction | Zone Size |
| 1:10 | 28.5 | mm. | 1 | 27 | mm. | 6 | 25 mm. |
| 1:20 | 26.5 | mm. | 2 | 30 | mm. | 7 | 23 mm. |
| 1:40 | 24 | mm. | 3 | 28.5 | mm. | 8 | 22 mm. |
| | | | 4 | 26 | mm. | 9 | 21 mm. |
| | | | 5 | 26 | mm. | 10 | 17.5 mm. |

The spent stream assayed 25 mm. without dilution and the water wash assayed 23 mm. without dilution.

Step D: Adsorption on a Non-Ionic Resin

Fractions 1 through 10 from Step C were combined and fed to a 45 liter bed of Amberlite XAD-2 adsorbent at pH 3.0 and at a flow rate of 5 liters per minute. The resin bed was washed with 90 liters of water at the same rate. The antibiotic was then eluted from the resin by a 25% solution of acetone and water at a flow rate of 5 liters per minute. Sixteen 5-gallon fractions were collected.

All fractions were assayed by disc-plate method against *Proteus vulgaris* as follows: The feed (190 liters) gave the following zone diameters:

| Feed Solution | |
|---|---|
| Dilution | Zone Size |
| 1:5 | 30 mm. |
| 1:10 | 27.5 mm. |
| 1:20 | 24.2 mm. |

The zone diameters of the eluate fractions are tabulated below:

| Eluate Fraction | | | Eluate Fraction | | |
|---|---|---|---|---|---|
| Fraction | Dilution | Zone Size | Fraction | Dilution | Zone Size |
| 1 | 1:10 | 20.5 mm. | 9 | 1:10 | 25 mm. |
| 2 | 1:10 | 29 mm. | 10 | 1:10 | 26.5 mm. |
| 3 | 1:10 | 29 mm. | 11 | 1:5 | 26 mm. |
| 4 | 1:10 | 29 mm. | 12 | 1:5 | 28 mm. |
| 5 | 1:10 | 28 mm. | 13 | 1:5 | 27.5 mm. |
| 6 | 1:10 | 27 mm. | 14 | 1:5 | 25 mm. |
| 7 | 1:10 | 26 mm. | 15 | 1:5 | 25 mm. |
| 8 | 1:10 | 26 mm. | 16 | 1:5 | 24.5 mm. |

The eluate fractions 2 through 16, supra, were combined and the acetone removed by vacuum evaporation to a final volume of 17.4 liters. The 17.4 liter concentrate was adjusted to pH 4.0 by ammonium hydroxide and freeze dried to yield 620 g. of Antibiotic 810A, i.e., a mixture consisting essentially of 7$\beta$-(D-5-amino-5-carboxyvaleramido)-3-($\alpha$-methoxy-p-sulfooxycinnamoyloxymethyl)-7-methoxy-3-cephem-4-carboxylic acid and 7$\beta$-(D-5-amino-5-carboxyvaleramido)-3-($\alpha$-methoxy-p-hydroxycinnamoyloxymethyl)-7-methoxy-3-cephem-4-carboxylic acid. This dry product had a bioassay potency of 320 mcg./ml. for a 25 mm. zone.

Step E: 7$\beta$-(D-5-amino-5-carboxyvaleramido)-3-($\alpha$-methoxy-p-hydroxycinnamoyloxymethyl)-7-methoxy-3-cephem-4-carboxylic Acid A 1 inch diameter chromatography column was packed to a bed height of 100 centimeters with DEAE Sephadex A-25 anion exchange resin in a system containing 0.5 M ammonium bromide and 0.05 M acetic acid. The mixture of Antibiotic 810A (10.0 g.) obtained in Step D was dissolved in 18 ml. of a solution of 0.5 M ammonium bromide and 0.05 M acetic acid and charged to the column. Eluting solution was pumped through the bed at a rate of 81 ml./hour and 10 ml. fractions of eluate were collected by machine. The eluate stream was monitored by a differential refractometer. The refractometer record showed mass peaks at tubes 19, 36, 79, 109 and 206. Disc plate assays against *Proteus vulgaris* (MB-838) were run on every third fraction using 0.5 inch diameter discs buffered at pH 7.0. The zone diameters are tabulated below: (Fractions 1 through 66 assayed zero.

| Fraction | Zone Diameter | Fraction | Zone Diameter | Fraction | Zone Diameter |
|---|---|---|---|---|---|
| 69 | 18 mm. | 122 | 29 | 204 | 40 + |
| 72 | 24 | 125 | 28 | 207 | 40 + |
| 75 | 26 | 128 | 27 | 210 | 40 + |
| 78 | 31 | 131 | 26 | 213 | 40 + |
| 81 | — | 134 | 24 | 216 | 40 + |
| 83 | 35 | 137 | 21 | 219 | 40 |
| 86 | 37 | 140 | 20 | 222 | 38 |
| 89 | 38 | 150 | 18 | 225 | 35 |
| 92 | 38 | 160 | 20 | 228 | 32 |
| 95 | 40 + | 170 | 29 | 231 | 31 |
| 98 | 40 + | 180 | 35 | 234 | 27 |
| 101 | 40 + | 183 | 38 | 237 | 24 |
| 104 | 40 + | 186 | 40 | 240 | 23 |
| 107 | 40 + | 189 | 40 + | 243 | 19 |
| 110 | 40 + | 192 | 40 + | 246 | 17 |
| 113 | 40 | 195 | 40 + | 249 | 0 |
| 116 | 38 | 198 | 40 + | 252 | 0 |
| 119 | 33 | 201 | 40 + | | |

Fractions 80 through 133 were combined and fractions 170 through 230 were combined.

A repeat of the above run was made and fractions 82-130 were combined and fractions 180-234 were combined.

The fractions containing the first active component from the two above runs were combined and adsorbed on a 100 ml. bed of Amberlite XAD-2 resin. The bed was washed with one volume of water and then eluted with three volumes of a 90% solution of methanol and water. The methanol was removed by vacuum evaporation and the aqueous concentrate was freeze dried to afford 810 mg. of a product identified as 7β-(D-5-amino-5-carboxyvaleramido)-3-(α-methoxy-p-hydroxycinnamoyloxymethyl)-7-methoxy-3-cephem-4-carboxylic acid. The bio-potency of this product determined by disc plate assay against *Proteus vulgaris* was 18 μg./ml. affording a 25 mm. zone. Analysis by ultraviolet adsorption gave the following characterizing data:

U.V. adsorption in 0.1 N HCL λmax. 305 $E_{1cm.}^{\%}$ 524

U.V. adsorption in 0.1 N NaOH λmax. 328 $E_{1cm.}^{\%}$ 564

Step F: 7β-(D-5-amino-5-carboxyvaleramido)-3-(α-methoxy-p-sulfooxycinnamoyloxymethyl)-7-methoxy-3-cephem-4-carboxylic Acid The fractions from the two runs on Sephadex A-25 containing the second active component were combined and adsorbed on a 100 ml. bed of Amberlite XAD-2 resin. The bed was washed with one volume of water and then eluted with three volumes of a 90% solution of methanol and water. The rich eluates were combined and methanol was removed by vacuum evaporation. The aqueous concentrate was freeze dried and yielded 720 mg. of 7β-(D-5-amino-5-carboxyvaleramido)-3-(α-methoxy-p-sulfooxycinnamoyloxymethyl)-7-methoxy-3-cephem-4-carboxylic acid (Ic). Analysis by ultraviolet adsorption gave the following characterizing data:

U.V. adsorption in 0.1 N HCl max. 287 mm. $E_{1cm.}^{\%}$ 432

U.V. adsorption in 0.1 N NaOH max. 280 mm. $E_{1cm.}^{\%}$ 432

EXAMPLE 6

Separation of 7β-(D-5-amino-5-carboxyvaleramido)-3-(α-methoxy-p-sulfooxycinnamoyloxymethyl)-7-methoxy-3-cephem-4-carboxylic Acid from the Antibiotic Mixture 810A The antibiotic mixture 810A comprising 7β-(D-5-amino-5-carboxyvaleramido)-3-(α-methoxy-p-sulfooxycinnamoyloxy-methyl)-7-methoxy-3-cephem-4-carboxylic acid (Ic) and 7β-(D-5-amino-5-carboxyvaleramido)-3-(α-methoxy-p-hydroxycinnamoyloxymethyl)-7-methoxy-3-cephem-4-carboxylic acid (20.0 g.) from Example 5, Step D, was dissolved in water (200 ml.) and the pH of the solution adjusted to 3.5. This solution was passed thru a 200 ml. bed of Amberlite IRA-68 anion exchange resin on the chloride cycle followed by the addition of 300 ml. of water wash. The bed was then eluted with 1 liter of 1% (v/v) formic acid in water. This was followed by the addition of two portions of dilute hydrochloric acid pH 0.95. The fed solution, spent and wash, and eluates 1, 2 and 3 were analyzed by paper electrophoresis at pH 4.0 run 1 hour at 1000 volts D.C. The papergram was dried, exposed to ammonia vapor to neutralize acid and incubated on a nutrient agar plate seeded with *Proteus vulgaris* (MB-838). Examination after 17 hours incubation at 37° C. showed two zones of inhibition in the feed material (in the direction of the anode), only a single component (slower of the two) in the spent and formic acid eluates and a single component in the second hydrochloric acid eluate corresponding with the faster component in the feed. The following table indicates total-solid and bioassay data:

| | Mass | Volume | Total Biological Units | Product(s) |
|---|---|---|---|---|
| Feed | 20 g. | 200 ml. | 60,000 units | Ia |
| Spent & Wash | 11.15 g. | 500 ml. | 7,500 units | — |
| Formic Acid Eluate | 4.52 g. | 1000 ml. | 20,000 units | — |
| 1st Hydrochloric Acid Eluate | — | 500 ml. | 1,000 units | — |
| 2nd Hydrochloric Acid Eluate | 2.10 g. | 500 ml. | 10,000 units | Ic |

The last fractions were recovered by adsorption on Amberlite XAD-2 resin to separate out 7β-(D-5-amino-5-carboxyvaleramido)-3-(α-methoxy-p-sulfooxycinnamoyloxymethyl)-7-methoxy-3-cephem-4-carboxylic acid (Ic) and this was eluted by a 50% solution of methanol and water to afford substantially pure product (Ic).

EXAMPLE 7

Separation of
7β-(D-5-amino-5-carboxyvaleramido)-3-(α-methoxy-p-sulfooxycinnamoyloxymethyl)-7-methoxy-3-cephem-4-carboxylic Acid from Antibiotic 810A The Antibiotic 810A mixture of 7β-(D-5-amino-5-carboxyvaleramido)-3-(α-methoxy-p-sulfooxycinnamoyloxymethyl)-7-methoxy-3-cephem-4-carboxylic acid (Ic) and 7β-(D-5-amino-5-carboxyvaleramido)-3-(α-methoxy-p-hydroxycinnamoyloxymethyl)-7-methoxy-3-cephem-4-carboxylic acid (5.0 g.) obtained according to Example 5, Step D, was dissolved in a 20% solution of acetone and water (20 ml.) and the pH adjusted to 4.0. This solution was fed to a 2 inch diameter × 100 cm. height bed of Amberlite XAD-2 adsorbent in 20% acetone and water solution. A solution of 20% acetone and water was pumped through the bed at a rate of 880 ml./hour and 20 ml. fractions were collected automatically.

Disc plate assays against Proteus vulgaris (MB-8 38) were run on every third fraction using 0.25 inch discs. The zone diameters are tabulated below:

| Fraction | Zone Diameter | Fraction | Zone Diameter | Fraction | Zone Diameter |
|---|---|---|---|---|---|
| 1–41 | 0 | 131 | 0 | 221 | 18 |
| 44 | 12 mm. | 134 | 0 | 224 | 18 |
| 47 | 22 | 137 | 0 | 227 | 18 |
| 50 | 25 | 140 | 8 | 230 | 17 |
| 53 | 29 | 143 | 11 | 233 | 17 |
| 56 | 31 | 146 | 13 | 236 | 15 |
| 59 | 35 | 149 | 13 | 239 | 15 |
| 62 | 30 | 152 | 15 | 242 | 15 |
| 65 | 28 | 155 | 15 | 245 | 15 |
| 68 | 27 | 158 | 16 | 248 | 14 |
| 71 | 25 | 161 | 17 | 251 | 14 |
| 74 | 24 | 164 | 18 | 254 | 14 |
| 77 | 21 | 167 | 17 | 257 | 13 |
| 80 | 20 | 170 | 18 | 260 | 13 |
| 83 | 19 | 173 | 20 | 263 | 12 |
| 86 | 16 | 176 | 21 | 266 | 12 |
| 89 | 14 | 179 | 21 | 269 | 12 |
| 92 | 13 | 182 | 21 | 272 | 11 |
| 95 | 13 | 185 | 21 | 275 | 11 |
| 98 | 13 | 188 | 22 | 278 | 10 |
| 101 | 13 | 191 | 23 | 281 | 10 |
| 104 | 14 | 194 | 23 | 284 | 9 |
| 107 | 13 | 197 | 23 | 287 | 8 |
| 110 | 13 | 200 | 22 | 290 | 0 |
| 113 | 11 | 203 | 24 | 293 | 0 |
| 116 | 10 | 206 | 24 | 296 | 0 |
| 119 | 9 | 209 | 24 | 299 | 0 |
| 122 | 8 | 212 | 24 | 302 | 0 |
| 125 | 8 | 215 | 24 | | |
| 128 | 8 | 218 | 19 | 330 | zero |

Fractions 44 through 90 were combined, acetone was removed by vacuum evaporation and the aqueous concentrate was freeze dried to yield 3.3 g. of crude 7β-(D-5-amino-5-carboxyvaleramido)-3-(α-methoxy-p-sulfooxycinnamoyloxymethyl)-7-methoxy-3-cephem-4-carboxylic acid (Ic).

Fractions 150 through 225 were combined and by similar treatment afforded 700 mg. of 7β-(D-5-amino-5-carboxyvaleramido)-3-(α-methoxy-p-hydroxycinnamoyloxymethyl)-7-methoxy-3-cephem-4-carboxylic acid.

A repeat of the above run afforded 3.1 g. of crude 7β-(D-5-amino-5-carboxyvaleramido)-3-(α-methoxy-p-sulfooxycinnamoyloxymethyl)-7-methoxy-3-cephem 4-carboxylic acid (Ic) and 400 mg. of 7β-(D-5-amino-5-carboxyvaleramido)-3-(β-methoxy-p-hydroxycinnamoyloxymethyl)-7-methoxy-3-cephem-4-carboxylic acid.

The two quantities of 7β-(D-5-amino-5-carboxyvaleramido)-3-(α-methoxy-p-sulfooxycinnamoyloxymethyl)-7-methoxy-3-cephem-4-carboxylic acid (Ic) obtained according to the foregoing method were combined and the 6.4 g. of material was charged to a 2 inch diameter × 100 cm. height bed of Amberlite XAD-2 adsorbent in a 5% solution of methanol and water. A 5% methanol and water solution was pumped through the bed at a flow rate of 880 ml./hour and 20 ml. fractions were collected automatically. Two hundred and eighty-seven fractions were collected and every fourth fraction was assayed by the disc-plate method against Proteus vulgaris (MB-838) using 0.25 inch discs. The assay results are tabulated below. Fractions 1 through 50 were not assayed.

| Fraction | Zone Size | Fraction | Zone Size |
|---|---|---|---|
| 51 | 23 mm. | 115 | 20 |
| 55 | 26 | 119 | 20 |
| 59 | 23 | 123 | 19 |
| 63 | 18 | 127 | 18 |
| 67 | 12 | 131 | 19 |
| 71 | 0 | 155 | 16 |
| 75 | 0 | 139 | 17 |
| 79 | 0 | 143 | 15 |
| 83 | 7 | 147 | 16 |
| 87 | 9 | 151 | 15 |
| 91 | 13 | 155 | 13 |
| 95 | 19 | 159 | 11 |
| 99 | 21 | 163 | 9 |
| 103 | 22 | 167 | 0 |
| 107 | 22 | 171 | 0 |
| 111 | 21 | 287 | zero |

Fractions 95 through 159 were combined, methanol vacuum evaporated, and the aqueous concentrate freeze dried to yield 700 mg. of 7β-(D-5-amino-5-carboxyvaleramido)-3-(α-methoxy-p-sulfooxycinnamoyloxymethyl)-7-methoxy-3-cephem-4-carboxylic acid (Ic). The ultra violet spectra of 7β-(D-5-amino-5-carboxyvaleramido)-3-(α-methoxy-p-sulfooxycinnamoyloxymethyl)-7-methoxy-3-cephem-4-carboxylic acid (Ic) gave the following adsorption data:

U.V. adsorption in 0.1 N HCl max. 285 $E_{1cm}$.% 160
U.V. adsorption in 0.1 N NaOH max. 277 $E_{1cm}$. 166

When assayed with 0.5 inch diameter discs by the disc-plate method against Proteus vulgaris the 7β-(D-5-amino-5-carboxyvaleramido)-3-(α-methoxy-p-sulfooxycinnamoyloxymethyl)-7-methoxy-3-cephem-4-carboxylic acid (Ic) sample gave a 25 mm. zone at 88 mcg./ml. and 7β-(D-5-amino-5-carboxyvaleramido)-3-(α-methoxy-p-hydroxycinnamoyloxymethyl)-7-methoxy-3-cephem-4-carboxylic acid gave a 25 mm. zone at 167 mcg/ml.

EXAMPLE 8

Antibiotic 842A

Step A: Shake Flask Production

A lyophilized tube of Streptomyces lactamdurans culture (MA-2908) was opened asceptically. The tube was then used to inoculate a 250 ml. baffled Erlenmeyer flask containing 50 ml. of nutrient Medium V by breaking the tube in sterile gauze and transferring the pellet asceptically into the flask. The Medium V has the following composition:

| Medium V: | |
|---|---|
| Yeast Autolysate (Ardamine) | 10.0 g. |
| Glucose | 10.0 g. |
| *Phosphate Buffer | 2.0 ml. |
| $MgSO_4 \cdot 7H_2O$ | 0.05 g. |

| | Medium V: | |
|---|---|---|
| | Distilled Water | 1000.0 ml. | pH 6.5

| *Phosphate Buffer: | |
|---|---|
| KH$_2$PO$_4$ | 91.0 g. |
| Na$_2$HPO$_4$ | 95.0 g. |
| Distilled Water | 1000.0 ml. |

This seed flask was shaken at 28° C. on a 220 rpm. rotary shaker with a 2 inch throw for 3 days. Five ml. aliquots (10% inoculum) of this growth were then transferred, using sterile pipettes, to four second-stage seed flasks of the same size and containing the same medium as described above and these flasks were then shaken in the manner indicated above. The second-stage seed flasks were then pooled asceptically into one flask and used to inoculate 11 2-liter baffled Erlenmeyer flasks, each containing 350 ml. of Medium IX with 2–3% inoculum using sterile pipettes. Medium IX has the following composition:

| Medium IX: | |
|---|---|
| Amber Yeast No. 300 | 10.0 g. |
| Distiller's Solubles | 20.0 g. |
| Dextrose | 10.0 g. |
| Distilled Water | 1000.0 ml. |
| pH 7.0 | |

The production flasks were then shaken at 28° C. on a 145 rpm. shaker with a 2 inch throw for 4 days. At the end of the incubation period the contents of 10 such flasks were combined and a sample was centrifuged to remove the mycelium.

The presence of Antibiotic 842A, i.e., the product 7β-(D-5-amino-5-carboxyvaleramido)-3-(carbamoyloxymethyl)-7-methoxy-3-cephem-4-carboxylic acid (Ib), in the broth was determined by agar diffusion assays performed with 0.5 inch filter paper discs soaked in the broth and set on the surface of assay plates containing 10 ml. of nutrient agar (Difco) plus 0.2% yeast extract (Di co) medium seeded with the bacterial inoculum. The zones of inhibition were measured in mm. after overnight incubation at 28° C. The assays of broth harvested after fermentation for 4 days showed an inhibition zone of 31.5 mm. diameter on plates seeded with *Vibrio percolans* (MB-1272).

Step B: Adsorption On An Anion Exchange Resin

The filtered broth was adjusted to pH 7.0 with dilute hydrochloric acid and 2900 ml. was adsorbed on 100 ml. of a strongly basic anion exchange resin having a styrenedivinylbenzene matrix (Dowex 1 × 2 chloride cycle resin) at 10 ml/minute. The spent was collected in 500 ml. fractions. The resin column was washed with water and eluted with 3% NH$_4$Cl in 90% methanol. The eluate was collected in 100 ml. fractions.

Disc plate assays against *Vibrio Percolans* (MB-1272) were run on all fractions; the zone diameters are tabulated below.

| Filtered Broth | | Spent Fraction | | Eluate Fraction | |
|---|---|---|---|---|---|
| Dilution | Zone Size | Fraction | Zone Size | Fraction | Zone Size |
| None | 26.5 mm. | 1. | 0 | 1. | 25 |
| 1:2 | 24 | 2. | 16 | 2. | 29 |
| 1:4 | 20 | 3. | 23 | 3. | 29 |
| | | 4. | 25 | 4. | 26.5 |
| | | 5. | 27 | 5. | 22 |
| | | 6. | 27 | 6. | 18 |
| | | | | 7. | 15 |
| | | | | 8–10. | 0 |

These assays indicate about 60% of the activity is in the spent and about 18% is in the eluates. This eluate is the ammonium salt of 842A. Furthermore, they indicate that the resin capacity is only two fractions or 10 column volumes of broth. Eluate fractions 1 through 4 were combined and concentrated to remove methanol. Spent fractions 3 through 6 were combined to give 1960 ml. of solution. An 1860 ml. portion of the solution was adjusted from pH 7.2 to 8.0 with dilute sodium hydroxide and adsorbed on 100 ml. of a strongly basic anion exchange resin having a styrene-divinylbenzene matrix (Dowex 1 × 2 chloride cycle resin) at 14 ml/minute. The spent was collected in four equal fractions and assays indicate that 5% of the activity was present. The column was washed with water and eluted with 5% aqueous sodium chloride. The eluate, which contains the sodium salt of 842A, was collected in 50 ml. fractions and assayed. The assays indicated that 90% of the activity was present in cuts 3 through 16 so these were combined.

Step C: Adsorption On A Cation Exchange Resin

A 50 ml. portion of a concentrate as prepared in Step B was diluted to 500 ml., adjusted from pH 8.8 to pH 2.0 with dilute hydrochloric acid and adsorbed on 25 ml. of a strongly acidic cation exchange resin of the sulfonate type having a styrene-divinylbenzene matrix (Dowex 50 × 2 hydrogen cycle resin) at 2.5 ml/minute. The column was washed with 25 ml. of water then eluted with 2% pyridine until the pH of the column effluent rose to pH 7 (54 ml.). Assays of the spent fraction and eluate indicated 9% of the activity in the spent and 90% in the eluate. The eluate was identified as the pyridinium salt of Antibiotic 842A.

The 842A product is amphoteric with an apparent isoelectric point at about pH 3.5. The product is unstable above pH 7 but stable at pH 1.5. The eluate thus obtained was adjusted to pH 8.0 with dilute sodium hydroxide and concentrated under vacuum to remove pyridine. The product thus obtained was identified as the monosodium salt of Antibiotic 842A. The molecular weight is 468 based on the empirical formula.

Analysis for C$_{16}$H$_{21}$N$_4$SO$_9$Na: Calc.: C,41.0%; H, 4.5%; N, 12.0%; S, 6.8%; O, 30.8%, Na, 4.9%. Found: C, 39.31%; H, 4.76%; N,11.16%; S, 6.46%; O, 34.12%; Na, 4.19%.

In in vitro studies this product, i.e., Antibiotic 842A, inhibits the growth of the following gram-negative bacteria: *Escherichia coli, Proteus vulgaris, Alcaligenes faecalis, Brucella bronchiseptica, Salmonella gallinarum, Vibrio percolans* and *Xanthomonas vesicatoria*. Also the product inhibits the growth of the following gram-positive bacteria: *Staphylococcus aureus, Sarcina lutea* and *Bacillus subtilis*.

In in vivo studies in mice Antibiotic 842A also exhibits the following activities. Administration was by subcutaneous injection. At the completion of the test period, usually 7 days after administration, the amount of product required to protect 50% of the mice ($ED_{50}$) from this otherwise fatal injection was calculated:

|  | $ED_{50}$ by Subcutaneous Route × Two Doses |
|---|---|
| Proteus vulgaris | 51 μg. |
| Proteus mirabilis | 276 μg. |
| *Proteus morganii 3202 | 276 μg. |
| Salmonella schottmuelleri | 103 μg. |
| Klebsiella pneumoniae AD | 125 μg. |
| Klebsiella pneumoniae B | 125 μg. |
| Paracolobactrum arizonae | 125 μg. |
| Escherichia coli | 200 μg. |
| Aerobacter aerogenes | 49 μg. |
| Pasteurella multocida | 57 μg. |
| Salmonella typhosa | 34 μg. |
| Diplococcus pneumoniae 2400 | 566 μg. |

*Cephaloridine and Cephalothin failed to protect at 4000 mg. × 2 doses

In addition to the aforementioned in vivo trials of the product a clinical isolate of Proteus morganii 356 which is resistant to cephalosporins and capable of degrading cephalosporin C, was employed in a mouse protection test performed in the same manner as reported above. The $ED_{50}$ for these tests is as follows:

| Infection | Antibiotic | $ED_{50}$ by Subcutaneous Route × 2 Doses (average of Two Trials) |
|---|---|---|
| Proteus morganii 356 | 842A | 273 μg. |
| Proteus morganii 356 | Cephalothin | >20,000 μg. |
| Proteus morganii 356 | Cephaloridine | 9,270 μg. |

EXAMPLE 9

Antibiotic 842A

Shake Flask Production:

The inoculum was prepared as described in Example 8. Two second-stage seed flasks were pooled and the broth used to inoculate (at 1 ml./flask) 62 Erlenmeyer flasks (250 ml.) each containing 50 ml. of Medium X. The Medium X has the following composition:

| Medium X: | |
|---|---|
| Staley's 4S-Soybean Meal | 30.0 g. |
| Distiller's Solubles | 7.5 g. |
| Cerelose | 20.0 g. |
| NaCl | 2.5 g. |
| $CaCO_3$ (after pH to 7.0) | 10.0 g. |
| Distilled Water | 1000.0 ml. |

The flasks were shaken at 28° C. on a 220 rpm. shaker with a 2 inch throw for 5 days. At the end of the incubation period the contents of 60 such flasks were combined and a sample was centrifuged to remove the mycelium.

The presence of Antibiotic 842A was determined by following the procedure described in Example 8 via agar diffusion assays performed on 0.5 inch filter paper assay discs. After incubation for 4 days, assay of broth gave an inhibition zone of 33 mm. versus Vibrio percolans (MB-1272).

EXAMPLE 10

Antibiotic 842A

Fermentation:

Stage 1: A lyophilized tube of Streptomyces lactamdurans culture (MA-2908) was used to inoculate 50 ml. of sterile Medium V in a baffled 200 ml. Erlenmeyer flask.

| Medium V: | |
|---|---|
| Yeast Autolysate (Ardamine) | 10.0 g. |
| Glucose | 10.0 g. |
| *Phosphate Buffer | 2.0 ml. |
| $MgSO_4 . 7H_2O$ | 0.05 g. |
| Distilled Water | 1000.0 ml. |
| pH - adjust to 6.5 using NaOH | |
| *Phosphate Buffer: | |
| $KH_2PO_4$ | 91.0 g. |
| $Na_2HPO_4$ | 95.0 g. |
| Distilled Water | 1000.0 ml. |

The inoculated flask was placed on a 220 rpm. rotary shaker with a 2 inch throw and incubated for 72 hours at 28° C.

Stage 2: An inoculum of 10.0 ml. of the resulting vegetative growth was then used to inoculate a 2-liter baffled Erlenmeyer flask containing 50 ml. of the sterilized Medium V described above. The inoculated flask was then placed on a 220 rpm. rotary shaker and incubated for 48 hours at 28° C.

Stage 3: The contents of the inoculum flask was then used to inoculate a 50 gallon stainless fermentor containing 160 liters of the same Medium V described above. The inoculated medium was incubated at 28° C. for 48 hours with agitation while maintaining an airflow of 3 cfm through the fermenting broth. During the fermentation period, small amounts of Polyglycol 2000 were added to control foaming.

Stage 4: An inoculum of 43 liters of the resulting growth was then used to inoculate a 200 gallon stainless steel fermentor containing 467 liters of a sterile Medium XII having the following composition:

| Medium XI: | |
|---|---|
| Amber Yeast No. 300 | 10.0 g. |
| Distiller's Solubles | 20.0 g. |
| Distilled Water | 1000.0 ml. |
| pH 7.0 | |

The fermentation was allowed to proceed at a temperature of 28° C. with agitation while maintaining an airflow of 10 cfm for 72 hours. During the fermentation an antifoam agent, Polyglycol 2000 was added in small quantities to prevent excessive foaming. The batch was harvested and activity was determined by disc plate assay. The fermentation broth was then filtered through diatomaceous earth at a pH of 7.8 and the product thus obtained was identified as 842A by following the procedure described in Example 8. Disc-plate assays of a 1:10 dilution gave an inhibition zone of 21.5 mm. v. Vibrio percolans (MB-1272).

EXAMPLE 11

Purification; Monosodium Salt of
7β-(D-5-Amino-5-Carboxyvaleramido)-3-(Carbamoyloxymethyl)-7-Methoxy-3-Cephem-4-Carboxylic Acid Adsorption on Carbon: Four fermentation batches harvested according to Example 8, were each adsorbed on 100 ml. of a strongly basic anion exchange resin having a styrenedivinylbenzene matrix (Dowex 1 × 2 chloride cycle resin) and eluted with 1% aqueous sodium chloride. The eluate was collected in 50 ml. fractions assayed. Eluate fractions from all four batches were adjusted to pH 5 with dilute hydrochloric acid and combined to give 4300 ml. of solution. 4200 ml. of this solution was stirred with 42 g. of carbon (Darco G-α) for ½ hour. The carbon was collected by filtration and washed with water. The filtrate and wash were void of activity. The carbon cake was eluted twice with a 1 liter portion of 60% aqueous acetone by stirring the mixture for ½ hour and filtering each time. The eluates were concentrated under vacuum to 108 ml. and 100 ml., respectively. Assays indicated that the first eluate contained 76% of the activity, 18 times as potent as the starting material and that the second contained 17% of the activity, 14 times as potent as the starting material. The two concentrates were combined and concentrated further to 61 ml. and adjusted from pH 4 to pH 5 with dilute sodium hydroxide. This concentrate contained 40 mg/ml. of dry solids and gave a 25 mm. zone against MB-1272 at a dilution of 1:100 (400 μg./ml.). The product was identified as the monosodium salt of 7β-(D-5-amino-5-carboxyvaleramido)-3-(carbamoyloxymethyl)-7-methoxy-3-cephem-4-carboxylic acid (Ib).

EXAMPLE 12

Purification; Monosodium Salt of 7β-(D-5-amino-5-Carboxyvaleramido)-3-(Carbamoyloxymethyl)-7-Methoxy-3-Cephem-4-Carboxylic Acid Separation on Gel: A 22 ml. portion of the eluate obtained according to Example 8, Step B, was adjusted to pH 7.0 with dilute sodium hydroxide and chromatographed on a column containing 388 ml. of Biogel P-2. The column was developed with water, the effluent monitored with a differential refractometer and 5 ml. fractions collected automatically and bioassayed. The bioactivity appeared in fractions 47 through 63 while sodium chloride appeared in fractions 62 through 72. Fractions 50 through 60 were pooled, reassayed and concentrated to dryness yielding 10.8 mg. of residue identified as the monosodium salt of 7β-(D-5-amino-5-carboxyvaleramido)-3-(carbamoyloxymethyl)-7-methoxy-3-cephem-4-carboxylic acid(Ib). On assay with *Vibrio percolans* this product gave a 25 mm. zone at 8 mcg./ml.

EXAMPLE 13

7β-(D-5-Amino-5-Carboxyvaleramido)-3-(Carbamoyloxymethyl)-7-methoxy-3-Cephem-4-Carboxylic Acid Modified Fermentation Process:
Step A: Slants A lyophilized tube of *Streptomyces lactamdurans* culture (MA-2908) was opened asceptically and the organism transferred to a medium of the following composition:

Medium XII:
1% Blackstrap Molasses
1% National Brewer's Yeast
2.5% Difco agar pH 7.0
Water to volume The slants are incubated for 7 days at 28° C. When stored in the cold, the slants are stable for more than 13 weeks.

Step B: Seed Stages: Two Stage System

First Seed: The first seed is inoculated directly from the slant of Step A to 40 ml. of 1% Primary Dried Yeast N.F., pH 7.0 (obtained from the Yeast Product Corporation) in a 250 ml. baffled Erlenmeyer flask. The flasks were then shaken on a 220 rpm. rotary shaker with a 2 inch throw at 28° C. for a period of from 2 to 3 days.

Second Seed: A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step C: Production Medium

The production medium contains per liter of distilled water: 30 g. distiller's solubles; 7.5 g. Primary Dried Yeast N.F. and 0.25% v/v Mobilpar-S defoamer. The medium is adjusted to pH 7.0 with a small amount of concentrated NaOH solution, dispensed into 250 ml. Erlenmeyer flasks and autoclaved for 15 or 20 minutes at 121° C. After cooling the medium received a 2.5% inoculum of the seed obtained in Step B. The time of incubation can vary from about 50 hours to 100 hours but an incubation period of about 72 hours is preferred. The volume of media in each flask can vary from 30 to 50 ml. but 40 ml. was used routinely. The level of inoculum can vary from 1 to 5%; but, in practice, a 2.5% level is generally employed.

Step D: Assay

When the fermentation was complete, the cells were removed by centrifugation and the broth was diluted with phosphate buffer, pH 7.0. The concentration of 7β-(D-5-amino-5-carboxyvaleramido)-3-(carbamoyloxymethyl)-7-methoxy-3-cephem-4-carboxylic acid in the fermentation broth was determined by the standard biological-disc assay method. The assay organism employed was *Vibrio percolans* (ATCC 8461). Filter paper discs are emersed into the diluted broths and placed on the surface of agar-containing Petri dishes that had been inoculated with the assay organism *Vibrio percolans* (ATCC 8461). Also placed on these Petri dishes are discs that had been dipped previously in standard solutions containing known concentrations of 842A. The discs were incubated overnight at 28° C. and the diameters of the zones of inhibition recorded. The concentration of 842A and the fermented broth is calculated by interpolation from the standard curve which relates zone diameter with the known concentrations of standard 842A solutions. By this procedure it was calculated that *Streptomyces lactamdurans* MB-2908 produced 78.6 μg./ml. of 842A in the modified fermentation process.

EXAMPLE 14

Purification; Monosodium Salt of 7β-(D-5-Amino-5-Carboxyvaleramido)-3-(Carbamoyloxymethyl)-7-Methoxy-3-Cephem-4-Carboxylic Acid The monosodium salt of 7β-(D-5-amino-5-carboxyvaleramido)-3-(carbamoyloxymethyl)-7-methoxy-3-cephem-4-carboxylic acid (1.0 g.) prepared according to Example 12 was dissolved in 20 ml. of 1% aqueous n-butanol and chromatographed on a column containing 2,530 ml. of Sephadex G-10, a modified dextran gel in bead form. The column was developed with 1% aqueous n-butanol at 10 ml/minute and 10.5 ml. fractions were collected automatically. The effluent was monitored with a recording refractometer and the fractions were bioassayed. The bioactivity appeared in fractions 99 through 122 and these were pooled and concentrated to dryness to yield 670 mg. of product containing primarily the monosodium salt of 7β-(D-5-amino-5-carboxyvaleramido)-3-(carbamoyloxymethyl)-7-methoxy-3-cephem-4-carboxylic acid.

The column was subsequently calibrated by chromatography on a mixture of Blue Dextran 2000 and sodium chloride under identical conditions. Blue Dextran 2000 was detected in fractions 85 through 93 and sodium chloride was detected in fractions 140 through 155, thus indicating that the bioactive product can be separated from impurities of this nature.

The novel compounds of this invention have been described as having the 5amino-5-carboxyvaleramido radical in the beta configuration with respect to the cephem nucleus. While this is based upon information currently available and is believed to be correct, applicants do not wish to be bound by this designation of spatial configuration in the event later information proves this to be incorrect.

The following organisms referred to in this specification are on deposit in the Culture Collection of the American Type Culture Collection where they are available under the following ATCC designations:

| | |
|---|---|
| *Escherichia coli* W-MB-60 | ATCC 9637 |
| *Proteus vulgaris* MB-838 | ATCC 21100 |
| *Alcalicenes faecalis* MB-9 | ATCC 212 |
| *Alcaligenes viscosus* MB-12 | ATCC 337 |
| *Vibrio percolans* MB-1272 | ATCC 8461 |
| *Bacillus subtilis* MB-964 | ATCC 6633 |

Also, in this specification several of the materials employed are referred to by trade name. These have the following composition and are available from the following suppliers:

Amber Yeast No. 300: a fraction of autolyzed brewers yeast; Amber Laboratories, Juneau, Wisconsin.

Mobil par-S: an oil base defoamer (composition unknown); Mobil Oil Company, 150 E. 42nd Street, New York, New York.

Polyglycol 2000: a defoamer; polypropylene glycol polymer having an average molecular weight of 2000; Dow Chemical Company, Midland, Michigan.

Biogel P-2: a gel filtration medium; a spherical polyacrylamide cross-linked with methylene bis-acrylamide; Bio-rad Laboratories, Richmond, California.

Dowex 50: a polystyrene nuclear sulfonic acid cation exchange resin; Dow Chemical Company, Midland, Michigan.

Analtech G.F. Plates: silica gel with calcium sulfate binder and a fluorescent indicator 250 micrometers in thickness; Analtech Inc., 100 South Justison Street, Wilmington, Delaware, 19801.

Whatman 1: qualitative, chromatographic paper having an average thickness of 0.005 inches and an approximate ash weight of 0.0005 mg. per 11 cm. circle; W. and R. Balston, LTD., Address: H. Reeve Angle & Co., Inc., 52 Duane Street, New York 7, N.Y.

Whatman 3 MM: chromatographic paper having a medium flow rate with a capacity twice that of Whatman 1; approximate ash weight of 0.0009 mg. per 11 cm. circle; W. and R. Balston, LTD., Address: H. Reeve Angle & Co., Inc., 52 Duane Street, New York 7, N.Y.

Camag S & S 2040-B: chromatographic paper; Camag Inc., 11830 West Ripley Avenue, Milwaukee, Wisconsin.

We claim:

1. The method for the preparation of 7β-(D-5-amino-5-carboxyvaleramido)-3-(carbamoyloxymethyl)-7-methoxy-3-cephem-4-carboxylic acid which comprises growing in an aqueous nutrient medium under aerobic conditions an actinomycete capable of producing the desired product wherein the actinomycete is Streptomyces lactamdurans NRRL 3802.

2. The method of claim 1 wherein the aqueous nutrient medium contains about 1 and 6% by weight of carbohydrate and between about 0.2 and 6% by weight of available nitrogen.

3. The method of claim 1 wherein the fermentation is conducted at a temperature in the range of from about 20° to 37° C.

4. The method of claim 1 wherein the pH of the aqueous nutrient medium is in the range of from about 6.0 to 8.0.

* * * * *